(12) United States Patent
van der Knaap et al.

(10) Patent No.: US 11,382,920 B2
(45) Date of Patent: Jul. 12, 2022

(54) THERAPEUTIC EFFECTS OF GUANABENZ TREATMENT IN VANISHING WHITE MATTER

(71) Applicant: Stichting VUmc, Amsterdam (NL)

(72) Inventors: Margo Sientje van der Knaap, Amsterdam (NL); Vivi Majella Heine, Amsterdam (NL); Gertrude Elise Maria Abbink, Amsterdam (NL)

(73) Assignee: Stichting VUmc, Amsterdam (NL)

( * ) Notice: Subject to any disclaimer, the term of this patent is extended or adjusted under 35 U.S.C. 154(b) by 0 days.

(21) Appl. No.: 16/610,191

(22) PCT Filed: May 4, 2018

(86) PCT No.: PCT/NL2018/050293
§ 371 (c)(1),
(2) Date: Nov. 1, 2019

(87) PCT Pub. No.: WO2018/203751
PCT Pub. Date: Nov. 8, 2018

(65) Prior Publication Data
US 2021/0106595 A1    Apr. 15, 2021

(30) Foreign Application Priority Data

May 4, 2017  (EP) .................................... 17169488

(51) Int. Cl.
| | | |
|---|---|---|
| *A61P 25/28* | (2006.01) | |
| *A61K 31/395* | (2006.01) | |
| *A61K 31/155* | (2006.01) | |
| *A61K 31/357* | (2006.01) | |
| *A61K 31/36* | (2006.01) | |
| *A61K 31/4168* | (2006.01) | |
| *A61K 31/44* | (2006.01) | |

(52) U.S. Cl.
CPC ........ *A61K 31/5545* (2017.08); *A61K 31/155* (2013.01); *A61K 31/357* (2013.01); *A61K 31/36* (2013.01); *A61K 31/4168* (2013.01); *A61K 31/44* (2013.01); *A61P 25/28* (2018.01)

(58) Field of Classification Search
CPC .................................................. A61K 31/5545
See application file for complete search history.

(56) References Cited

FOREIGN PATENT DOCUMENTS

| WO | 2016001389 A1 | 1/2016 |
| WO | WO2016/001389 | * 1/2016 |

OTHER PUBLICATIONS

International Search Report and Written Opinion in corresponding International Patent Application No. PCT/NL2018/050293 dated Oct. 5, 2018. 16 pages.

Dooves et al. "Bergmann glia translocation: a new disease marker for vanishing white matter identifies therapeutic effects of Guanabenz treatment." Neuropathology and Applied Neurobiology (2017). 13 pages.
Bonkowsky JL, Nelson C, Kingston JL, Filloux FM, Mundorff MB, Srivastava R. "The burden of inherited leukodystrophies in children". Neurol 2010; 75: 718-725. 8 pages.
Vanderver A, Hussey H, Schmidt JL, Pastor W, Hoffman HJ. "Relative incidence of inherited white matter disoders in childhood to acquired pediatric demyelinating disorders". Semin Pediatr Neurol 2012; 19: 219-223. 5 pages.
Gulati S, Jain P, Chakrabarty B, Kumar A, Gupta N, Kabra M. "The spectrum of leukodystrophies in children: Experience at a tertiary care centre for North India". Ann Indian Acad Neurol 2016; 19: 332-338. 14 pages.
Van der Knaap MS, Pronk JC, Scheper GC. "Vanishing white matter disease". Lancet Neurol 2006; 5: 413-423. 11 pages.
Bugiani M, Boor I, Powers JM, Scheper GC, van der Knaap MS. "Leukoencephalopathy with vanishing white matter: a review". J Neuropathol Exp Neurol 2010; 69: 987-996. 10 pages.
Bugiani M, Boor I, van Kollenburg B, Postma N, Polder E, van Berkel C, van Kesteren RE, Windrem MS, Hol EM, Scheper GC, Goldman SA, van der Knaap MS. "Defective glial maturation in vanishing white matter disease". J Neuropathol Exp Neurol 2011; 70: 69-82. 14 pages.
Dooves S, Bugiani M, Postma NL, Polder E, Land N, Horan ST, van Deijk AL, van der Kreeke A, Jacobs G, Vuong C, Klooster J, Kamermans M, Wortel J, Loos M, Wisse LE, Scheper GC, Abbink TE, Heine VM, van der Knaap MS. "Astrocytes are central in the pathomechanisms of vanishing white matter". J Clin Invest 2016; 126: 1512-1524. 13 pages.
Leegwater PA, Vermeulen G, Könst AA, Naidu S, Mulders J, Visser A, Kersbergen P, Mobach D, Fonds D, van Berkel CG, Lemmers RJ, Frants RR, Oudejans CB, Schutgens RB, Pronk JC, van der Knaap MS. "Subunits of the translation intiation factor eIF2B are mutant in leukoencephalopathy with vanishing white matter". Nat Genet 2001: 29; 383-388. 6 pages.
Van der Knaap MS, Wolf NI, Heine VM. "Leukodystrophies five new things". Neurol Clin Pract 2016; 6:1-9. 10 pages.
Dooves S, van der Knaap MS, Heine VM. "Stem cell therapy for white matter disorders: don't forget the microenvironment!" J Inherit Metab Dis 2016; 39: 513-518. 6 pages.
Goldman SA, Nedergaard M, Windrem MS. "Glial progenitor cell-based treatment and modeling of neurological disease". Science 2012; 338: 491-495. 6 pages.
Maeder ML, Gersbach CA. "Genome-editing technologies for gene and cell therapy". Mol Ther 2016; 24: 430-446. 17 pages.
Ricca A, Rufo N, Ungari S, Morena F, Martino S, Kulik W, Alberizzi V, Bolino A, Bianchi F, Del Carro U, Biffi A, Gritti A. "Combined gene/cell therapies provide long-term and pervasive rescue of multiple pathological symptoms in a murine model of globoid cell leukodystrophy". Hum Mol Genet 2015: 24; 3372-3389. 18 pages.

(Continued)

*Primary Examiner* — Marcos L Sznaidman
(74) *Attorney, Agent, or Firm* — Leason Ellis LLP

(57) ABSTRACT

The invention relates to Guanabenz or an analogue thereof for use in the treatment and to methods of treatment of a subject that has vanishing white matter (VWM), comprising administering the compound Guanabenz or an analogue thereof to the subject in need thereof. Also provided are methods with which the success of a medical intervention in a subject with VWM can be determined. Such methods comprise quantifying the translocation of Bergmann glia into the molecular layer in the cerebellum in a suitable sample of the subject. The sample is typically a post mortem sample.

5 Claims, 10 Drawing Sheets

(56) References Cited

OTHER PUBLICATIONS

Bugiani M, Postma N, Polder E, Dieleman N, Scheffer PG, Sim FJ, van der Knaap MS, Boor I. "Hyaluronan accumulation and arrested oligodendrocyte progenitor maturation in vanishing white matter disease". Brain 2013; 136: 209-222. 14 pages.

Tribouillard-Tanvier D, Béringue V, Desban N, Gug F, Bach S, Voisset C, Galons H, Laude H, Vilette D, Blondel M. "Antihypertensive drug guanabenz is active in vivo against both yeast and mammalian prions". Plos One 2008; 3: e1981. 9 pages.

Tsaytler P, Harding HP, Ron D, Bertolotti A. "Selective inhibition of a regulatory subunit of protein phosphatase 1 restores proteostasis". Science 2011; 332: 91-94. 5 pages.

Wang L, Popko B, Tixier E, Roos RP. "Guanabenz, which enhances the unfolded protein response, ameliorates mutant SOD1-induced amyotrophic lateral sclerosis". Neurobiol Dis 2014; 71: 317-324. 8 pages.

Ng SY, Soh BS, Rodriguez-Muela N, Hendrickson DG, Price F, Rinn JL, Rubin LL. "Genome-wide RNA-seq of human motor neurons implicates selective ER stress activation in spinal muscular atrophy". Cell Stem Cell 2015; 17: 569-584. 17 pages.

Way SW, Podojil JR, Clayton BL, Zaremba A, Collins TL, Kunjamma RB, Robinson AP, Brugarolas P, Miller RH, Miller SD, Popko B. "Pharmaceutical integrated stress response enhancement protects oligodendrocytes and provides a potential multiple sclerosis therapeutic". Nat Commun 2015; 6: 6532. 13 pages.

Dash PK, Hylin MJ, Hood KN, Orsi SA, Zhao J, Redell JB, Tsvetkov AS, Moore AN. "Inhibition of eukaryotic initiation factor 2 alpha phosphatase reduces tissue damage and improves learning and memory after experimental traumatic brain injury. J". Neurotrauma 2015; 32: 1608-1620. 13 pages.

Vieira FG, Ping Q, Moreno AJ, Kidd JD, Thompson K, Jiang B, et al. (2015) "Guanabenz Treatment Accelerates Disease in a Mutant SOD1 Mouse Model of ALS". PLoS ONE 10(8): e0135570. https://doi.org/10.1371/journal.pone.0135570. 15 pages.

Saraswat Ohri S, Mullins A, Hetman M, Whittemore SR (2014) "Inhibition of GADD34, the Stress-Inducible Regulatory Subunit of the Endoplasmic Reticulum Stress Response, Does Not Enhance Functional Recovery after Spinal Cord Injury". PLoS ONE 9(11): e109703. https://doi.org/10.1371/journal.pone. 0109703. 10 pages.

Van der Voom JP, van Kollenburg B, Bertrand G, van Haren K, Scheper GC, Powers JM, van der Knaap MS. "The Unfolded Protein Response in Vanishing White Matter Disease". Journal of Neuropathology & Experimental Neurology, vol. 64 2005, pp. 770-775. https://doi.org/10.1097/01.jnen. 0000178446.41595.3a. 6 pages.

Kapur M, Monaghan CE, and Ackerman SL, "Regulation of mRNA Translation in Neurons—A Matter of Life and Death". Neuron vol. 96, 2017, pp. 616-637. https://doi.org/10.1016/j.neuron.2017.09. 057. 22 pages.

Heine VM, Rowitch DH. "Hedgehog signaling has a protective effect in glucocorticoid-induced mouse neonatal brain injury through an 11 beta HSD2-dependent mechanism". J Clin Invest 2009; 119: 267-277. 11 pages.

Rivero-Gutiérrez B, Anzola A, Martinez-Augustin O, de Medina FS. "Stain-free detection as loading control alternative to Ponceau and housekeeping protein immunodetection in Western blotting". Anal Biochem 2014; 467: 1-3. 3 pages.

Gürtler A, Kunz N, Gomolka M, Hornhardt S, Friedl AA, McDonald K, Kohn JE, Posch A. "Stain-free technology as a normalization tool in Western blot analysis". Anal Biochem 2013; 433: 105-111. 7 pages.

Buffo A, Rossi F. "Origin, lineage and function of cerebellar glia". Prog Neurobiol 2013; 109: 42-63. 22 pages.

Patro N, Naik A, Patro IK. "Differential temporal expression of S100 beta in developing rat brain". Front Cell Neurosci 2015; 9: 87. 12 pages.

Ajtai BM, Kálmán M. "Glial fibrillary acidic protein expression but no glial demarcation follows the lesion in the molecular layer of the cerebellum". Brain Res 1998; 802: 285-288. 4 pages.

Adorjan I, Bindics K, Galgoczy P, Kalman M. "Phases of intermediate filament composition in Bergmann glia following cerebellar injury in adult rat". Exp Brain Res 2014; 232: 2095-2104. 10 pages.

Lafarga M, Berciano MT, Saurez Andres MA, Berciano J. "Reactive astroglia-neuron relationships in the human cerebellar cortex: a quantitative, morphological and immunocytochemical study in Creutzfeldt-Jakob disease". Int J Dev Neurosci 1993; 11: 199-213. 15 pages.

Komine O, Nagaoka M, Watase K, Gutmann DH, Tanigaki K, Honjo T, Radtke F, Saito T, Chiba S, Tanaka K. "The monolayer formation of Bergmann glial cells is regulated by Notch/RBP-J signaling". Dev Biol 2007; 311: 238-250. 13 pages.

Wang X, Imura T, Sofroniew MV, Fushiki S. "Loss of adenomatous polyposis coli in Bergmann glia disrupts their unique architecture and leads to cell nonautonomous neurodegeneration of cerebellar Purkinje neurons". Glia 2011; 59: 857-868. 12 pages.

Das I, Krzyzosiak A, Schneider K, Wrabetz L, D'Antonio M, Barry N, Sigurdardottir A, Bertolotti A. "Preventing proteostasis diseases by selective inhibition of a phosphatase regulatory subunit". Science 2015; 348: 239-242. 5 pages.

Wisse LE, Penning R, Zaal EA, et al., "Proteomic and metabolomic analyses of vanishing white matter mouse astrocytes reveal deregulation of er functions". Front Cell Neurosci, 2017, 11. 16 pages.

Sekine Y, Zyryanova A, Crespillo-Casado A, et al., "Stress responses. Mutations in a translation initiation factor identify the target of a memory-enhancing compound". Science, 2015, 348, 1027-30. 5 pages.

Sidrauski C, Tsai JC, Kampmann M, et al., "Pharmacological dimerization and activation of the exchange factor eif2b antagonizes the integrated stress response", Elife, 2015, 4, e07314. 27 pages.

Dooves S BM, Wisse LE, Abbink TEM, van der Knaap MS, Heine VM., "Bergmann glia translocation: A new disease marker for vanishing white matter identifies therapeutic effects of guanabenz treatment". Neuropathology and Applied Neurobiology, 2017, in press, doi: 10.1111/nan.12411. 13 pages.

Crespillo-Casado A, Chambers JE, Fischer PM, et al., "Ppp1r15a-mediated dephosphorylation of eIF2α is unaffected by sephin1 or guanabenz". Elife, 2017, 6. 29 pages.

Abdulkarim,et al. "Guanabenz sensitizes pancreatic β cells to lipotoxic endoplasmic reticulum stress and apoptosis." Endocrinology, 2017, 5 pages.

Baez, et al. "Dose-Ranging Study to Delineate the Additive Antihypertensive Effect of Guanabenz and Captopril." Antihypertensive Therapy, 1991, 8 pages.

Banerjee, et al. "Protein Folding Activity of the Ribosome (PFAR)—A Target for Antiprion Compounds." Viruses 2014, 6, 3907-3924, doi:10.3390/v6103907, 18 pages.

Barbezier, et al. "Antiprion drugs 6-aminophenanthridine and guanabenz reduce PABPN1 toxicity and aggregation in oculopharyngeal muscular dystrophy." EMBO Mol Med 3, 35-49, DOI 10.1002/emmm. 201000109, 2010, 15 pages.

Bella, et al. "Protein misfolding, amyotrophic lateral sclerosis and guanabenz: protocol for a phase II RCT with futility design (ProMISe trial)." BMJ Open 2017;7:e015434. doi:10.1136/bmjopen-2016-015434, 9 pages.

Bella, et al. "The unfolded protein response in amyotrophic later sclerosis: results of a phase 2 trial." Brain : a journal of neurology vol. 144,9 (2021): 2635-2647. doi:10.1093/brain/awab167, 38 pages.

Benmerzouga, et al. "Guanabenz repurposed as an antiparasitic with activity against acute and latent toxoplasmosis." Antimicrobial agents and chemotherapy vol. 59,11 (2015): 6939-45. doi:10.1128/AAC.01683-15, 7 pages.

Bogorad, et al. "Novel mechanisms of eIF2B action and regulation by eIF2α phosphorylation." Nucleic acids research vol. 45,20 (2017): 11962-11979. doi:10.1093/nar/gkx845, 18 pages.

Capuzzi, et al. "Inhibition of hepatic cholesterol and triglyceride synthesis by guanabenz acetate." Journal of cardiovascular pharmacology vol. 6 Suppl 5 (1984): S847-52. doi:10.1097/00005344-198400065-00024, 6 pages.

(56) References Cited

OTHER PUBLICATIONS

Chen, et al. "Sephin1, which prolongs the integrated stress response, is a promising therapeutic for multiple sclerosis." Brain : a journal of neurology vol. 142,2 (2019): 344-361. doi:10.1093/brain/awy322, 18 pages.

Cheng, et al. "Loss of Oca2 disrupts the unfolded protein response and increases resistance to endoplasmic reticulum stress in melanocytes." Pigment cell & melanoma research vol. 26,6 (2013): 826-34. doi:10.1111/pcmr.12158, 9 pages.

Clement, et al. "Microsomal catalyzed N-hydroxylation of guanabenz and reduction of the N-hydroxylated metabolite: characterization of the two reactions and genotoxic potential of guanoxabenz." Chemical research in toxicology vol. 9,4 (1996): 682-8. doi:10.1021/tx9502047, 7 pages.

Colahan, et al. "The effect of adrenergic suppression induced by guanabenz administration on exercising thoroughbred horses." Equine veterinary journal. Supplement ,36 (2006): 262-6. doi:10.1111/j.2042-3306.2006.tb05550.x, 5 pages.

Crespillo-Casado, et al. "PPP1R15A-mediated dephosphorylation of eIF2α is unaffected by Sephin1 or Guanabenz." eLife vol. 6 e26109. Apr. 27, 2017, doi:10.7554/eLife.26109, 29 pages.

"Common Terminology Criteria for Adverse Events (CTCAE)." Version 5.0, U.S. Department of Health and Human Services,National Institutes of Health, National Cancer Institute, Nov. 27, 2017, 147 pages.

Das, et al. "Preventing proteostasis diseases by selective inhibition of a phosphatase regulatory subunit." Science (New York, N.Y.) vol. 348,6231 (2015): 239-42. doi:10.1126/science.aaa4484, 5 pages.

Dash, et al. "Inhibition of Eukaryotic Initiation Factor 2 Alpha Phosphatase Reduces Tissue Damage and Improves Learning and Memory after Experimental Traumatic Brain Injury." Journal of neurotrauma vol. 32,20 (2015): 1608-20. doi:10.1089/neu.2014.3772, 13 pages.

Dooves, et al. "Bergmann glia translocation: a new disease marker for vanishing white matter identifies therapeutic effects of Guanabenz treatment." Neuropathology and applied neurobiology vol. 44,4 (2018): 391-403. doi:10.1111/nan.12411, 13 pages.

Dos Reis, et al. "Mode of action of the antiprion drugs 6AP and GA on ribosome assisted protein folding." Biochimie vol. 93,6 (2011): 1047-54. doi:10.1016/j.biochi.2011.03.002, 8 pages.

Dubrow, et al. "Safety and efficacy of guanabenz in hypertensive patients with moderate renal insufficiency." Journal of clinical hypertension vol. 1,4 (1985): 322-5, 5 pages.

Fardghassemi, et al. "Rescue of ATXN3 neuronal toxicity in Caenorhabditiselegans by chemical modification of endoplasmic reticulum stress." Disease models & mechanisms vol. 10,12 1465-1480. Dec. 19, 2017, doi:10.1242/dmm.029736, 16 pages.

Guanabenz—FDA prescribing information, side effects and uses, https://www.drugs.com/pro/guanabenz.html, 2016, 8 pages.

Fullwood, et al. "Targeting phosphorylation of eukaryotic initiation factor-2α to treat human disease." Progress in molecular biology and translational science vol. 106 (2012): 75-106. doi:10.1016/B978-0-12-396456-4.00005-5, 33 pages.

Fusade-Boyer, et al. "Evaluation of the Antiviral Activity of Sephin1 Treatment and Its Consequences on eIF2α Phosphorylation in Response to Viral Infections." Frontiers in immunology vol. 10 134. Feb. 12, 2019, doi:10.3389/fimmu.2019.00134, 12 pages.

Grenfell, R F. "Double-blind study of guanabenz acetate in hypertensive patients." Southern medical journal vol. 76,2 (1983): 199-201. doi:10.1097/00007611-198302000-00014, 3 pgaes.

Guanabenz—DrugBank. https://www.drugbank.ca/drugs/DB00629. 2020, 6 pages.

Gumeni, et al. "Hereditary Spastic Paraplegia and Future Therapeutic Directions: Beneficial Effects of Small Compounds Acting on Cellular Stress." Frontiers in neuroscience vol. 15 660714. May 6, 2021, doi:10.3389/fnins.2021.660714, 16 pages.

Hall, et al. "Guanabenz overdose." Annals of internal medicine vol. 102,6 (1985): 787-8. doi:10.7326/0003-4819-102-6-787, 2 pages.

Halliday, et al. "Partial restoration of protein synthesis rates by the small molecule ISRIB prevents neurodegeneration without pancreatic toxicity." Cell death & disease vol. 6,3 e1672. Mar. 5, 2015, doi:10.1038/cddis.2015.49, 9 pages.

Hamamura, et al. "In vitro and in silico analysis of an inhibitory mechanism of osteoclastogenesis by salubrinal and guanabenz." Cellular signalling vol. 27,2 (2015): 353-62. doi:10.1016/j.cellsig.2014.11.020, 10 pages.

Hamamura, et al. "Suppression of osteoclastogenesis through phosphorylation of eukaryotic translation initiation factor 2 alpha." Journal of bone and mineral metabolism vol. 31,6 (2013): 618-28. doi:10.1007/s00774-013-0450-0, 11 pages.

Harkins, J Daniel et al. "The detection and biotransformation of guanabenz in horses: a preliminary report." Veterinary therapeutics : research in applied veterinary medicine vol. 4,2 (2003): 197-209.

Hashimoto, et al. "Therapeutic effects of evening administration of guanabenz and clonidine on morning hypertension: evaluation using home-based blood pressure measurements." Journal of hypertension vol. 21,4 (2003): 805-11. doi:10.1097/00004872-200304000-00025, 7 pages.

Hayashi, et al. "Guanabenz, an antihypertensive centrally acting alpha2-agonist, suppresses morning elevations in aggregation of human platelets." Journal of cardiovascular pharmacology vol. 37,1 (2001): 89-93. doi:10.1097/00005344-200101000-00010, 5 pages.

Ho, et al. "Guanabenz Sensitizes Glioblastoma Cells to Sunitinib by Inhibiting GADD34-Mediated Autophagic Signaling." Neurotherapeutics : the journal of the American Society for Experimental NeuroTherapeutics vol. 18,2 (2021): 1371-1392. doi:10.1007/s13311-020-00961-z, 22 pages.

Holland, et al. "Effect of guanabenz and hydrochlorothiazide on blood pressure and plasma renin activity." Journal of clinical pharmacology vol. 21,4 (1981): 133-9. doi:10.1002/j.1552-4604.1981.tb05690.x, 7 pages.

Holmes, et al. "Guanabenz. A review of its pharmacodynamic properties and therapeutic efficacy in hypertension." Drugs vol. 26,3 (1983): 212-29. doi:10.2165/00003495-198326030-00003, 20 pages.

Hood, et al. "Endoplasmic Reticulum Stress Contributes to the Loss of Newborn Hippocampal Neurons after Traumatic Brain Injury." The Journal of neuroscience : the official journal of the Society for Neuroscience vol. 38,9 (2018): 2372-2384. doi:10.1523/JNEUROSCI.1756-17.2018, 13 pages.

Igaki, et al. "The effective inhibition of the Maillard reaction by guanabenz acetate, and its relevance to the prevention of diabetic complications." Clinica chimica acta; international journal of clinical chemistry vol. 199,1 (1991): 113-5. doi:10.1016/0009-8981(91)90015-5, 3 pages.

Minqing, et al. "Regulation of PERK-eIF2α signalling by tuberous sclerosis complex-1 controls homoeostasis and survival of myelinating oligodendrocytes." Nature Communications. 7. 12185. 10.1038/ncomms12185, 2016, 14 pages.

Perego, Jessica et al. "Guanabenz inhibits TLR9 signaling through a pathway that is independent of eIF2α dephosphorylation by the GADD34/PP1c complex." Science signaling vol. 11,514 eaam8104. Jan. 23, 2018, doi:10.1126/scisignal.aam8104, 14 pages.

Perego, Jessica et al. "Guanabenz Prevents d-Galactosamine/Lipopolysaccharide-Induced Liver Damage and Mortality." Frontiers in immunology vol. 8 679. Jun. 13, 2017, doi:10.3389/fimmu.2017.00679, 11 pages.

Sidrauski, Carmela et al. "Pharmacological brake-release of mRNA translation enhances cognitive memory." eLife vol. 2 e00498. May 28, 2013, doi:10.7554/eLife.00498, 22 pages.

Ruiz, Asier et al. "Sephin1 Protects Neurons against Excitotoxicity Independently of the Integrated Stress Response." International journal of molecular sciences vol. 21,17 6088. Aug. 24, 2020, doi:10.3390/ijms21176088, 11 pages.

Rutkowski, D Thomas, and Randal J Kaufman. "That which does not kill me makes me stronger: adapting to chronic ER stress." Trends in biochemical sciences vol. 32,10 (2007): 469-76. doi:10.1016/j.tibs.2007.09.003, 8 pages.

Shah, R S et al. "Guanabenz effects on blood pressure and noninvasive parameters of cardiac performance in patients with hypertension." Clinical pharmacology and therapeutics vol. 19,6 (1976): 732-7. doi:10.1002/cpt1976196732, 6 pages.

(56) References Cited

OTHER PUBLICATIONS

Shearer, C M, and N J DeAngelis. "Guanabenz degradation products and stability assay." Journal of pharmaceutical sciences vol. 68,8 (1979): 1010-2. doi:10.1002/jps.2600680824, 3 pages.

Sica, Domenic. "Centrally Acting Antihypertensive Agents: An Update. Journal of clinical hypertension." (Greenwich, Conn.). 9. 399-405 (2007). 10.1111/j.1524-6175.2007.07161.x, 7 pages.

Yanpallewar, Sudhirkumar U et al. "Alpha2-adrenoceptor blockade accelerates the neurogenic, neurotrophic, and behavioral effects of chronic antidepressant treatment." The Journal of neuroscience : the official journal of the Society for Neuroscience vol. 30,3 (2010): 1096-109. doi:10.1523/JNEUROSCI.2309-09.2010, 31 pages.

Sun, Xiaotian et al. "Guanabenz promotes neuronal survival via enhancement of ATF4 and parkin expression in models of Parkinson disease." Experimental neurology vol. 303 (2018): 95-107. doi:10.1016/j.expneurol.2018.01.015, 31 pages.

Takigawa, Shinya et al. "Guanabenz Downregulates Inflammatory Responses via eIF2α Dependent and Independent Signaling." International journal of molecular sciences vol. 17,5 674. May 5, 2016, doi:10.3390/ijms17050674, 12 pages.

"Problems of drug dependence, 1983. Proceedings of the 45th annual scientific meeting, The Committee on Problems of Drug Dependence, Inc." NIDA research monograph vol. 49 (1984): 1-448, 469 pages.

Thompson, Kaitlyn Koenig, and Stella E Tsirka. "Guanabenz modulates microglia and macrophages during demyelination." Scientific reports vol. 10,1 19333. Nov. 9, 2020, doi:10.1038/s41598-020-76383-w, 12 pages.

"Myelin Repair Foundation and NIH to Study Guanabenz for MS." May 7, 2015, 2 pages.

Tribouillard-Tanvier, Déborah et al. "Antihypertensive drug guanabenz is active in vivo against both yeast and mammalian prions." PloS one vol. 3,4 e1981. Apr. 23, 2008, doi:10.1371/journal.pone.0001981, 9 pages.

Tribouillard-Tanvier, Déborah et al. "Protein folding activity of ribosomal RNA is a selective target of two unrelated antiprion drugs." PloS one vol. 3,5 e2174. May 14, 2008, doi:10.1371/journal.pone.0002174, 14 pages.

Tsaytler, Pavel et al. "Selective inhibition of a regulatory subunit of protein phosphatase 1 restores proteostasis." Science (New York, N.Y.) vol. 332,6025 (2011): 91-4. doi:10.1126/science.1201396, 5 pages.

Vaccaro, Alexandra et al. "Pharmacological reduction of ER stress protects against TDP-43 neuronal toxicity in vivo." Neurobiology of disease vol. 55 (2013): 64-75. doi:10.1016/j.nbd.2013.03.015, 12 pages.

Vieira, Fernando G et al. "Guanabenz Treatment Accelerates Disease in a Mutant SOD1 Mouse Model of ALS." PloS one vol. 10,8 e0135570. Aug. 19, 2015, doi:10.1371/journal.pone.0135570, 15 pages.

Voisset, Cécile et al. "The various facets of the protein-folding activity of the ribosome." Biotechnology journal vol. 6,6 (2011): 668-73. doi:10.1002/biot.201100021, 6 pages.

Voisset, Cécile et al. "Tools for the study of ribosome-borne protein folding activity." Biotechnology journal vol. 3,8 (2008): 1033-40. doi:10.1002/biot.200800134, 8 pages.

Walker, B R et al. "Comparative antihypertensive effects of guanabenz and clonidine." The Journal of international medical research vol. 10,1 (1982): 6-14. doi:10.1177/030006058201000102, 9 pages.

Walker, B R et al. "Effects of placebo versus guanabenz on hypertensive out-patients." The Journal of international medical research vol. 8,5 (1980): 303-13. doi:10.1177/030006058000800501, 11 pages.

Walker, B R et al. "Guanabenz and methyldopa on hypertension and cardiac performance." Clinical pharmacology and therapeutics vol. 22,6 (1977): 868-74. doi:10.1002/cpt1977226868, 7 pages.

Walson, P D et al. "Guanabenz for adolescent hypertension." Pediatric pharmacology (New York, N.Y.) vol. 4,1 (1984): 1-6, 9 pages.

Wang, Lijun et al. "Guanabenz, which enhances the unfolded protein response, ameliorates mutant SOD1-induced amyotrophic lateral sclerosis." Neurobiology of disease vol. 71 (2014): 317-24. doi:10.1016/j.nbd.2014.08.010, 8 pages.

Way, Sharon W et al. "Pharmaceutical integrated stress response enhancement protects oligodendrocytes and provides a potential multiple sclerosis therapeutic." Nature communications vol. 6 6532. Mar. 13, 2015, doi:10.1038/ncomms7532, 13 pages.

Weidler, D J et al. "Dose-response relationship of single oral doses of guanabenz in hypertensive patients." Journal of cardiovascular pharmacology vol. 6 Suppl 5 (1984): S762-5. doi:10.1097/00005344-198400065-00007, 4 pages.

Jiang, H-Q et al. "Guanabenz delays the onset of disease symptoms, extends lifespan, improves motor performance and attenuates motor neuron loss in the SOD1 G93A mouse model of amyotrophic lateral sclerosis." Neuroscience vol. 277 (2014): 132-8. doi:10.1016/j.neuroscience.2014.03.047, 7 pages.

Julien, Carl et al. "Conserved pharmacological rescue of hereditary spastic paraplegia-related phenotypes across model organisms." Human molecular genetics vol. 25,6 (2016): 1088-99. doi:10.1093/hmg/ddv632, 12 pages.

Kang, Hyo Jeong et al. "Guanabenz Acetate Induces Endoplasmic Reticulum Stress-Related Cell Death in Hepatocellular Carcinoma Cells." Journal of pathology and translational medicine vol. 53,2 (2019): 94-103. doi:10.4132/jptm.2019.01.14, 10 pages.

Kluyskens, Y, and J Snoeck. "Comparison of guanabenz and clonidine in hypertensive patients." Current medical research and opinion vol. 6,9 (1980): 638-43. doi:10.1185/03007998009109502, 6 pages.

Konrad, Christian et al. "Inhibitors of eIF2α dephosphorylation slow replication and stabilize latency in Toxoplasma gondii." Antimicrobial agents and chemotherapy vol. 57,4 (2013): 1815-22. doi:10.1128/AAC.01899-12, 8 pages.

Kurko, Dalma et al. "Analysis of functional selectivity through G protein-dependent and -independent signaling pathways at the adrenergic α(2C) receptor." Brain research bulletin vol. 107 (2014): 89-101. doi:10.1016/j.brainresbull.2014.07.005, 13 pages.

Lasseter, K C et al. "Pharmacokinetics of guanabenz in patients with impaired liver function." Journal of cardiovascular pharmacology vol. 6 Suppl 5 (1984): S766-70. doi:10.1097/00005344-198400065-00008, 5 pages.

Leary, W P et al. "Evaluation of the efficacy and safety of guanabenz versus clonidine." South African medical journal = Suid-Afrikaanse tydskrif vir geneeskunde vol. 55,3 (1979): 83-5. , 3 pages.

Malerba, Alberto et al. "Pharmacological modulation of the ER stress response ameliorates oculopharyngeal muscular dystrophy." Human molecular genetics vol. 28,10 (2019): 1694-1708. doi:10.1093/hmg/ddz007, 15 pages.

Martinez, Gabriela et al. "Endoplasmic reticulum proteostasis impairment in aging." Aging cell vol. 16,4 (2017): 615-623. doi:10.1111/acel.12599, 9 pages.

Martynowicz, Jennifer et al. "Guanabenz Reverses a Key Behavioral Change Caused by Latent Toxoplasmosis in Mice by Reducing Neuroinflammation." mBio vol. 10,2 e00381-19. Apr. 30, 2019, doi:10.1128/mBio.00381-19, 15 pages.

McMahon, F G et al. "Guanabenz in essential hypertension." Clinical pharmacology and therapeutics vol. 21,3 (1977): 272-7. doi:10.1002/cpt1977213272, 6 pages.

Meacham, R H et al. "Disposition of 14C-guanabenz in patients with essential hypertension." Clinical pharmacology and therapeutics vol. 27,1 (1980): 44-52. doi:10.1038/clpt.1980.7, 9 pages.

Meacham, R H et al. "Pharmacokinetic disposition of guanabenz in the rhesus monkey." Drug metabolism and disposition: the biological fate of chemicals vol. 9,6 (1981): 509-14, 6 pages.

Meacham, R H et al. "Relationship of guanabenz concentrations in brain and plasma to antihypertensive effect in the spontaneously hypertensive rat." The Journal of pharmacology and experimental therapeutics vol. 214,3 (1980): 594-8, 5 pages.

Mockel, Anais et al. "Pharmacological modulation of the retinal unfolded protein response in Bardet-Biedl syndrome reduces apoptosis and preserves light detection ability." The Journal of biological chemistry vol. 287,44 (2012): 37483-94. doi:10.1074/jbc.M112.386821, 13 pages.

(56) References Cited

OTHER PUBLICATIONS

Montazeri, Mahbobeh et al. "Activities of anti-Toxoplasma drugs and compounds against tissue cysts in the last three decades (1987 to 2017), a systematic review." Parasitology research vol. 117,10 (2018): 3045-3057. doi:10.1007/e00436-018-6027-z, 13 pages.
Nakajima, Shotaro et al. "eIF2α-Independent Inhibition of TNF-α-Triggered NF-κB Activation by Salubrinal." Biological & pharmaceutical bulletin vol. 38,9 (2015): 1368-74. doi:10.1248/bpb.b15-00312, 7 pages.
Nakatsuka, M et al. "Metabolism-based inactivation of penile nitric oxide synthase activity by guanabenz." Drug metabolism and disposition: the biological fate of chemicals vol. 26,5 (1998): 497-501, 5 pages.
Nash, D T. "Clinical trial with guanabenz, a new antihypertensive agent." Journal of clinical pharmacology vol. 13,10 (1973): 416-21. doi:10.1002/j.1552-4604.1973.tb00188.x, 7 pages.
Neuber, Christiane et al. "Guanabenz interferes with ER stress and exerts protective effects in cardiac myocytes." PloS one vol. 9,6 e98893. Jun. 3, 2014, doi:10.1371/journal.pone.0098893, 9 pages.
Nevin, Zachary S et al. "Modeling the Mutational and Phenotypic Landscapes of Pelizaeus-Merzbacher Disease with Human iPSC-Derived Oligodendrocytes." American journal of human genetics vol. 100,4 (2017): 617-634. doi:10.1016/.ajhg.2017.03.005, 18 pages.
Ng, Shi-Yan et al. "Genome-wide RNA-Seq of Human Motor Neurons Implicates Selective ER Stress Activation in Spinal Muscular Atrophy." Cell stem cell vol. 17,5 (2015): 569-84. doi:10.1016/j.stem.2015.08.003, 17 pages.

Nguyen, Phu Hai et al. "Structure-activity relationship study around guanabenz identifies two derivatives retaining antiprion activity but having lost α2-adrenergic receptor agonistic activity." ACS chemical neuroscience vol. 5,10 (2014): 1075-82. doi:10.1021/cn5001588, 8 pages.
Noguchi, S et al. "Guanabenz-mediated inactivation and enhanced proteolytic degradation of neuronal nitric-oxide synthase." The Journal of biological chemistry vol. 275,4 (2000): 2376-80. doi:10.1074/jbc.275.4.2376, 6 pages.
Norman, Kenneth, and Thomas M. Nappe. "Alpha Receptor Agonist Toxicity." StatPearls, StatPearls Publishing, Aug. 11, 202, 6 pages.
Ohri, Sujata Saraswat et al. "Inhibition of GADD34, the stress-inducible regulatory subunit of the endoplasmic reticulum stress response, does not enhance functional recovery after spinal cord injury." PloS one vol. 9,11 e109703. Nov. 11, 2014, doi:10.1371/journal.pone.0109703, 10 pages.
Osborn, Maire F et al. "Guanabenz (Wytensin™) selectively enhances uptake and efficacy of hydrophobically modified siRNAs." Nucleic acids research vol. 43,18 (2015): 8664-72. doi:10.1093/nar/gkv942, 9 pages.
Peng, Xiaofei et al. "Impact of GADD34 on Apoptosis of Tonsillar Mononuclear Cells from IgA Nephropathy Patients by Regulating Eif2α Phosphorylation." Cellular physiology and biochemistry : international journal of experimental cellular physiology, biochemistry, and pharmacology vol. 50,6 (2018): 2203-2215. doi:10.1159/000495061, 13 pages.
Rogers, Guanabenz Overdose, Annals of Internal Medicine, p. 445, vol. 104, No. 3. Mar. 1986. 10 pages.

* cited by examiner

A

B

A

A

B

C

D

THERAPEUTIC EFFECTS OF GUANABENZ TREATMENT IN VANISHING WHITE MATTER

CROSS-REFERENCE TO RELATED PATENT APPLICATIONS

This application is a U.S. National Stage Application under 35 U.S.C. § 371 of International Patent Application No. PCT/NL2018/050293, filed May 4, 2018, which claims the benefit of priority to European Patent Application number 17169488.8 4 filed May 4, 2017, both of which are incorporated by reference in their entireties. The International Application was published on Nov. 8, 2018, as International Publication No. WO 2018/203751 A1.

The invention relates to the treatment of vanishing white matter (VWM). The invention in particular relates to the use of guanabenz or an analogue thereof in the treatment of VWM.

Brain white matter disorders (WMDs) comprise a large group of different disorders, genetic or acquired, all preferentially affecting brain white matter. The genetic brain white matter disorders are collectively called "leukodystrophies". They are devastating disorders, for which better treatments are needed. We focus on developing new therapies for Vanishing White Matter (VWM), a severe leukodystrophy. Leukodystrophies are rare to exceedingly rare, but collectively have an incidence of approximately 1 in 7,500 live births [1]. VWM is one of the more common leukodystrophies [1-3]. VWM patients show chronic progressive ataxia and spasticity with rapid worsening after stressors like head trauma and fever [4]. Survival time post-diagnosis is correlated with age at disease onset: neonates presenting with VWM have a severe disease course and live only a few months. Patients with a classical early childhood onset generally live for a few years post-diagnosis, while patients with the adult-onset form of VWM may live for decades [4]. Previous studies showed that the astrocytes and oligodendrocytes in the white matter are selectively affected, remain immature and fail in their mature function of, for instance, myelin production (oligodendrocytes) and scar tissue formation (astrocytes) [5, 6]. It was shown that astrocytes are central in the pathophysiology of VWM and that the oligodendrocyte maturation defect is probably secondary to astrocyte dysfunction [7]. VWM patients have mutations in the EIF2B1-5 genes encoding the five subunits (α-ε) of eukaryotic translation initiation factor 2B (eIF2B) [8]. eIF2B is the guanine nucleotide-exchange factor for eIF2. eIF2 is part of the ternary initiation complex, which is involved in the start of the translation of all mRNAs into proteins. If guanosine-5'-triphosphate (GTP) is bound to eIF2, it is active and can form an active initiation complex. The conversion of GTP to guanosine diphosphate (GDP) produces energy necessary in the process of translation initiation. eIF2-GDP is inactive. eIF2B catalyzes the exchange of GDP for GTP, after which eIF2-GTP can again form an active initiation complex, ready for the translation of a new mRNA. So, eIF2B is conditional for the presence of active initiation complexes and with that conditional for protein production. In addition to being indispensable for mRNA translation per se, the activity of eIF2B also determines the rate of mRNA translation/protein production, especially as part of cellular stress responses (the integrated stress response [ISR] as part of the unfolded protein response [UPR]). During cell stress, protein synthesis must be shut down. Different types of cell stress trigger the phosphorylation of eIF2. When phosphorylated, eIF2 binds and inactivates eIF2B. The downstream effect of decreased eIF2B activity is decreased mRNA translation and protein synthesis in general, but upregulated translation of some specific mRNAs, depending on characteristics of these mRNAs. Some of these upregulated proteins are transcription factors that further determine the fate of the cell. The best known of these is ATF4. Thus, decreased eIF2B activity activates the downstream part of cell stress pathways. VWM patients have mutations in one of the five subunits of eIF2B. In VWM, mutations in eIF2B decrease its activity and with that cause chronic activation of cell stress pathways. Abnormal activation of cell stress pathways has been demonstrated to selectively occur in brain white matter astrocytes and oligodendrocytes [4]. The reason for the selective sensitivity of the affected astrocytes and oligodendrocytes is not known. A theory is that the chronic activation of cell stress pathways with over-expression or under-expression of specific mRNAs/proteins contains the explanation for the cell specificity.

Several strategies to treat patients with WMDs have been suggested [9, 10] and have prospects for VWM patients. Cell replacement studies in animal models of myelin disease received much attention [11] and give possibilities for future clinical studies. The development of treatments based on gene therapy, either involving ex vivo or in vivo gene targeting strategies, regained attention after the development of safer viral constructs and new gene editing techniques [12]. As these different treatment options potentially target different aspects of the disease, multimodal therapeutic strategies might be most effective [9, 10], as indeed shown in an animal study for Krabbe disease [13]. Since recent studies indicate that factors secreted by VWM astrocytes into the extracellular matrix [14] or culture media [7] inhibit oligodendrocyte progenitor cell maturation [7], modulation of the white matter microenvironment might be another facet of multimodal therapy strategies for VWM specifically or for WMDs generally [10].

To assess treatment efficacy, models that representatively mimic disease and allow quantitative assessment of the disease state are essential. Recently developed mouse models for VWM, carrying homozygous mutations in the Eif2b5 ($2b5^{ho}$) or Eif2b4 ($2b4^{ho}$) gene, replicate many features of the human disease including ataxia, shortened lifespan, and astrocytic and myelin abnormalities [7]. To objectively address effectiveness of treatment options in these VWM models, proper disease markers are needed. A good disease marker should be quantitative, easy to assess, sensitive to both worsening and improvement, and show a faster response to interventions than the clinical phenotype. We have previously identified cell counts of nestin-positive astrocytes in the corpus callosum as a disease marker for VWM [7]. Increased expression of intermediate filament nestin [6, 7], which under normal conditions is predominantly present in immature astrocytes and neural stem cells, is a hallmark of astrocyte pathology in VWM. The number of nestin-positive astrocytes in the corpus callosum is quantifiable and easy to assess. Increased nestin counts in the corpus callosum of VWM mice are apparent at the first disease stages, before the mice display clinical signs, and the counts increase further during disease progression, making them a quantitative measure of disease severity. However, it is not known whether counts of nestin positive astrocytes drop with improvement and this still needs to be tested. Patients are often diagnosed and treated after the earliest disease stage. We therefore looked for additional disease markers that are related to intermediate and later disease stages to facilitate studies in those stages in our mouse models.

The Bergmann glia constitute an easy identifiable astrocytic population in the cerebellum. They are important for cerebellar cortical layering and Purkinje cell functioning. We previously showed that Bergmann glia translocate from the Purkinje cell layer, where their normal position is, into the molecular layer in both human VWM patients and VWM mice [7]. In previous studies we showed that white matter astrocytes remain immature in VWM. In the present invention we further assessed the maturation status of Bergmann glia by staining with radial glia cell marker 2 (RC2) and nestin antibodies. Furthermore, we quantified Bergmann glia translocation, analyzed changes in Bergmann glia translocation over the disease course and tested this translocation as a new VWM disease marker to determine treatment efficacy.

In the present invention we determined that compounds such as Guanabenz can be used in treatment strategies for VWM patients. Guanabenz, an agonist for the α-2 adrenergic receptor, has been used to treat arterial hypertension for 30 years without major side effects [15]. Recent discoveries indicate that Guanabenz has α-2 adrenergic receptor independent functions and can also regulate eIF2B activity indirectly through regulating the phosphorylation status of eIF2 [16]. As explained above, eIF2B activity regulates translation initiation, especially under cellular stress conditions. For instance, when the amount of un- or misfolded proteins inside the endoplasmic reticulum increases, the cell stress pathway called "unfolded protein response" (UPR) is activated. The UPR orchestrates adaptive mechanisms to recover the protein-folding status during cellular stress. Upon UPR activation, eIF2 (p-eIF2) is phosphorylated; p-eIF2 binds and inactivates eIF2B, which is the rate-limiting factor in mRNA translation/protein synthesis. Inactivated eIF2B leads to inhibition of general protein synthesis, but also to activation of the transcription factor ATF4. One of the downstream effects of activated ATF4 is activation of GADD34, which dephosphorylates eIF2, thereby restoring eIF2B activity. Guanabenz is thought to inhibit GADD34, thereby prolonging eIF2 phosphorylation and eIF2B inhibition. In cells that have normal amounts of eIF2B guanabenz is suggested to delay recovery during cellular stress by prolonging eIF2 phosphorylation, and thereby adjusting protein synthesis rates to manageable levels [16]. However, in VWM, in which the activity of eIF2B is already decreased because of mutations, Guanabenz would be expected to have a detrimental rather than beneficial effect.

Some studies showed a protective effect of Guanabenz in animal models of a range of brain disorders, in which the UPR is activated, like prion disease [15], amyotrophic lateral sclerosis [17], spinal muscular atrophy [18], multiple sclerosis [19] and traumatic brain injury [20]. In spite of the fact that negative results are typically not easily published, it was also shown that guanabenz treatment aggravates disease in a mutant SOD1 mouse model of ALS and does not enhance functional recovery after spinal cord injury [21, 22]. The authors conclude that inhibition of GADD34, the target of guanabenz, is not sufficient to overcome the UPR and/or ER stress-mediated pathology in these disease models. Guanabenz treatment is also discussed in US2016/0015659 and in WO2016/001389. The US application is by the same author as reference 19. WO2016/001389 describes proteopathies and/or disorders associated with accumulation of misfolded and/or unfolded proteins and the use of particular guanabenz analogues in the treatment of such disorders. Neither of these references specifically discloses the use of guanabenz for the treatment of VWM.

Leukodystrophies comprise a large number of diseases that share the symptom of degeneration of the white matter in the brain. The underlying genetic mutations are, however, very diverse. The genetic mutations that cause VWM disease are all in the eIF2B protein. This protein is central to translation initiation/protein synthesis and pivotal in the ISR and UPR. The ISR/UPR is affected in VWM (Van der Voorn et al., 2005 [23]). Van der Voorn et al conclude that: "it is therefore not clear if and how VWM mutations can lead to accumulation of misfolded proteins in the endoplasmic reticulum and activation of the UPR" (last column of the discussion on page 774)." The authors explain that eIF2B catalyzes the GDP-GTP exchange on eIF2, which is a necessary step in the initiation of translation. Patients already have a reduced activity of the eIF2B protein and are thus expected to have reduced translation. Additionally, in VWM the ATF4 transcription response is chronically activated by the decreased eIF2B activity, probably contributing to the disease. The skilled person would therefore question whether the effect of Guanabenz, which is to aggravate the inhibition of translation and the activation of the downstream ATF4 transcription response by inhibiting eIF2a dephosphorylation through inhibiting GADD34, would help in the case of VWM, because in VWM translation is already inhibited and the ATF4 transcription response is already activated.

Kapur et al (2017 [24]) explain that: "Given the function of eIF2B, one would predict that mutations diminishing its activity would result in decreased levels of eIF2-GTP-Met-tRNAi ternary complex, reducing global translation and increasing translation of uORF-containing transcripts. Consistent with this prediction, levels of ATF4 and its downstream target CHOP (C/EBP-homologous protein, DDIT) were increased in the brains of VWM patients (van der Voorn et al., 2005)" [23]. The activation of the ISR/UPR in VWM patients raises the interesting possibility that rapid progression of the disease after febrile infection or head trauma may be due to a stress-induced increase in the level of S51-phosphorylated eIF2a (p-eIF2a) that synergizes with the otherwise relatively subtle effects of eIF2B mutations on the availability of the ternary complex. Further studies are needed to determine whether dysregulation of global translation contributes to pathogenesis in VWM ([24] left column page 619). Thus Kapur et al are of the opinion that the rapid progression of the disease after febrile infection or head trauma can be the result of a stress-induced increase in the level of S51-phosphorylated eIF2a (p-eIF2a) and that this "synergizes with the otherwise relatively subtle effects of eIF2B mutations on the availability of the ternary complex". Kapur et al suggest that relief of rapid progression would be possible if the stress-induced increase in the level of p-eIF2a is inhibited or removed. This is precisely the function of GADD34. This protein dephosphorylates p-eIF2a and thus counterbalances the increase of p-eIF2a. Following this teaching GADD34 activity should be increased for the benefit of VWM and not reduced. The in vitro results as disclosed herein confirm the above mentioned expected outcome of guanabenz treatment. Chronic activation of the ISR pushes the cell towards stress induced death. However, in the present invention it was found that the situation is different in vivo. There we show that guanabenz effectively and transiently reduces phosphorylation of eIF2alpha.

In the present invention a new quantitative marker for VWM was developed. The level of the marker varies with varying disease severity. The marker is sensitive to treatment using the FDA-approved drug Guanabenz. We developed an assay to quantify Bergmann glia translocation in mice and patients. VWM mice treated with Guanabenz from 2- to 10-months-of-age exhibited marked improvement on different VWM disease markers when compared to saline treated controls.

SUMMARY OF THE INVENTION

The invention provides the compound guanabenz or an analogue thereof for use in the treatment of VWM.

The compound preferably comprises a structural formula I:

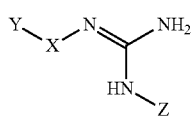

Formula I or a structural formula II:

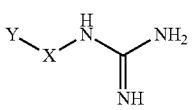

Formula II or a derivative that has a hydroxyl group in place of hydrogen on a terminal nitrogen wherein $X = O_m - C_n - N_p$ wherein m is 0 or 1; n is 0; 1 or 2 and p is 0 or 1; and wherein $Y =$ is a 6-8 membered substituted or unsubstituted carbocyclic or heterocyclic ring; and wherein Z=H or OH.

The invention also provides a method of treatment of a subject that has a VWM, the method comprising administering the compound guanabenz or an analogue thereof to the subject in need thereof.

Also provided is a method for determining the effect of a treatment of an individual with VWM, the method comprising quantifying the translocation of Bergmann glia into the molecular layer in the cerebellum.

DETAILED DESCRIPTION OF THE INVENTION

The invention provides guanabenz or an analogue thereof for use in the treatment of VWM.

The compound guanabenz has the structural formula III

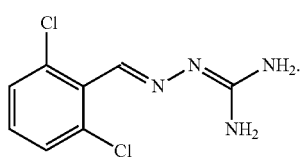

formula III

The analogue compound guanfacine has the structural formula IV

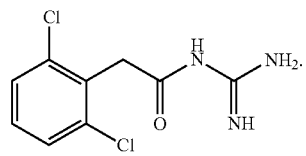

formula IV

Various other analogue compounds of guanabenz have been described. These include clonidine, guanacline, guanadrel, guanazodine, guanethidine, guanochlor, guanoxabenz and guanoxan. Preferred analogues of guanabenz comprise a 2, 6 dichlorosubstituted phenyl group. In a preferred embodiment the analogue has a hydroxyl group in place of hydrogen on a terminal nitrogen. An example of such an analogue is guanoxabenz. The compound guanabenz or analogue thereof preferably has the structural formula I:

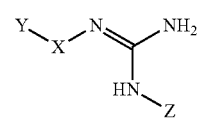

Formula I or a structural formula II:

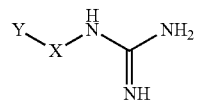

Formula II or a derivative that has a hydroxyl group in place of hydrogen on a terminal nitrogen wherein $X = O_m - C_n - N_p$ wherein m is 0 or 1; n is 0; 1 or 2 and p is 0 or 1;

wherein $Y =$ is a 6-8 membered substituted or unsubstituted carbocyclic or heterocyclic ring; and wherein Z=H or OH. In a preferred embodiment $Y =$ is a 6 membered substituted or unsubstituted carbocyclic ring. In a preferred embodiment the group Y is a phenyl, preferably a substituted phenyl. Y is preferably a 2,6-dichloro substituted phenyl.

X is preferably $O_m - C_n - N_p$ wherein m is 0; n is 0; 1 or 2 and p is 0 or 1. When n is 1 it is preferred that either m or p=1. In a preferred embodiment m=0, n=1 and p=1. In group X a bond between O and C; C and C; and C and N can be saturated or unsaturated. In X the atoms O; C and N can have side groups. The side groups are preferably all H, also when one or more of the bonds between the atoms O; C and N are double bonds.

The invention also provides a method of treatment of a subject that has VWM, the method comprising administering the compound guanabenz or an analogue thereof to the subject in need thereof. The subject is preferably a human subject.

Also provided is a method for determining the effect of a treatment of an individual with VWM, the method comprising quantifying the translocation of Bergmann glia from the Purkinje cell layer into the molecular layer in the cerebellum in a sample of said individual. The sample is obtained by biopsy of the cerebellum. Such a method is typically not diagnostic as suitable samples cannot be obtained without inducing irreparable damage to the brain. The sample is therefore typically a post mortem sample. The individual can be a human or a test animal. The method for determining the effect of treatment can be used to test the effect of treatment in human individuals, however, in humans the effect can also and probably even better be assessed using clinical parameters. Such clinical parameters include but are not limited to time-to-event analysis determined with Kaplan Meier curves and the Cox Mantel log-rank test. One can think of survival and neurological handicap, quantifiable by quality of life and handicap scales. The method for determining the effect of treatment is preferably performed with test animals. The quantifiable nature of the method is an important advantage. The test animal is typically a mammal, preferably a lab animal such as a mouse, a rat.

The compound guanabenz or the analogue compound thereof can be administered in various ways. The compound is typically given orally in the form of a pill or capsule. Suitable starting dose is 4 mg orally twice a day. Maintenance dose is typically 4 to 8 mg orally twice a day. The dose can be increased to 32 mg twice a day. The indicated dosage is preferred. A higher or lower dosage is encompassed herein. Lower dosages are typically associated with reduced side effects. Higher dosages are associated with increased side effects. The effect of the compound depends on the dosage given. The indicated dosage and ranges are typical for use in human adults and are given for the compound guanabenz. The dosing of an analogue can be adjusted using the above values as a guideline. For various specifically mentioned analogues, adequate dosages are provided in the art. The dosage for attaining the hypertension ameliorating effects are typically also suited for attaining the VWM treating effects as mentioned herein. Dosages can also be defined based on the weight of the subject to be treated. This is typically done for children. A suitable dosage based on the weight of the subject is: 50 ug/kg/day-1 mg/kg/day, a preferred range is 0.1-1 mg/kg/day. Another preferred range is 0.125-0.5 mg/kg/day.

On the basis of the in vivo mouse data, we expect that guanabenz ameliorates the disease in VWM patients, slowing the disease course, reducing the occurrence of episodes of rapid deterioration and prolonging life expectancy. Specifically, we expect guanabenz to prolong the time patients can walk without or with support and increase 2-year-survival. By slowing the disease course, handicap will be delayed and quality of life will be increased.

The effect of guanabenz can best be assessed by clinical parameters, including survival, time to lose walking without or with support and validated handicap and quality of life scales. Additionally, MRI of the brain can be used to monitor the disease, especially by using quantitative parameters that reflect degree of disruption of white matter integrity.

EXAMPLES

Example 1

Figure 1:
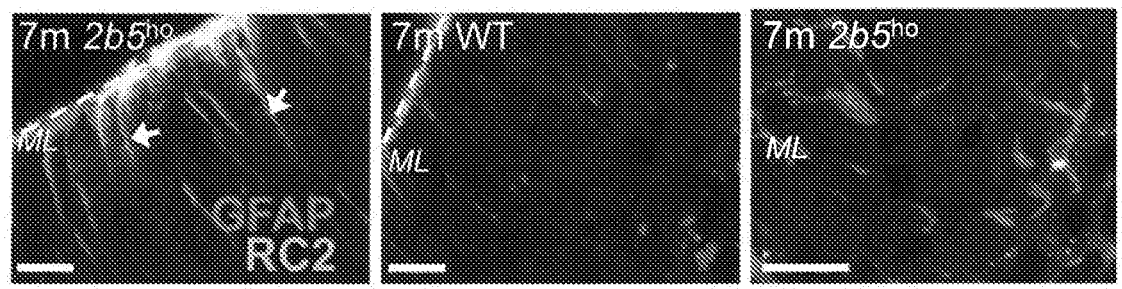
FIG. 1. Bergmann glia in VWM mice express markers of immaturity. (A) Bergmann glia of the cerebellum of 7-month-old VWM ($2b5^{ho}$) mice are immunopositive for the radial glia marker RC2, and often show an abnormal morphology with short processes that are retracted from the pial membrane. (B) nestin expression in Bergmann glia is observed in 5- and 7-month-old $2b5^{ho}$ mice, but not in 2-month-old $2b5^{ho}$ mice or wild type (WT) mice. The green staining that is observed in the picture of the 2-month-old $2b5^{ho}$ mice and the 2- and 5-month-old WT mice is non-specific staining of blood vessels, that does not co-localize with GFAP staining. Large, closed arrows indicate regions with double staining; small, open arrows indicate non-specific nestin staining. ML=molecular layer, PCL=Purkinje cell layer, GCL=granule cell layer. Scale bar A=25 μm; scale bar B=50 μm.
Figure 1:
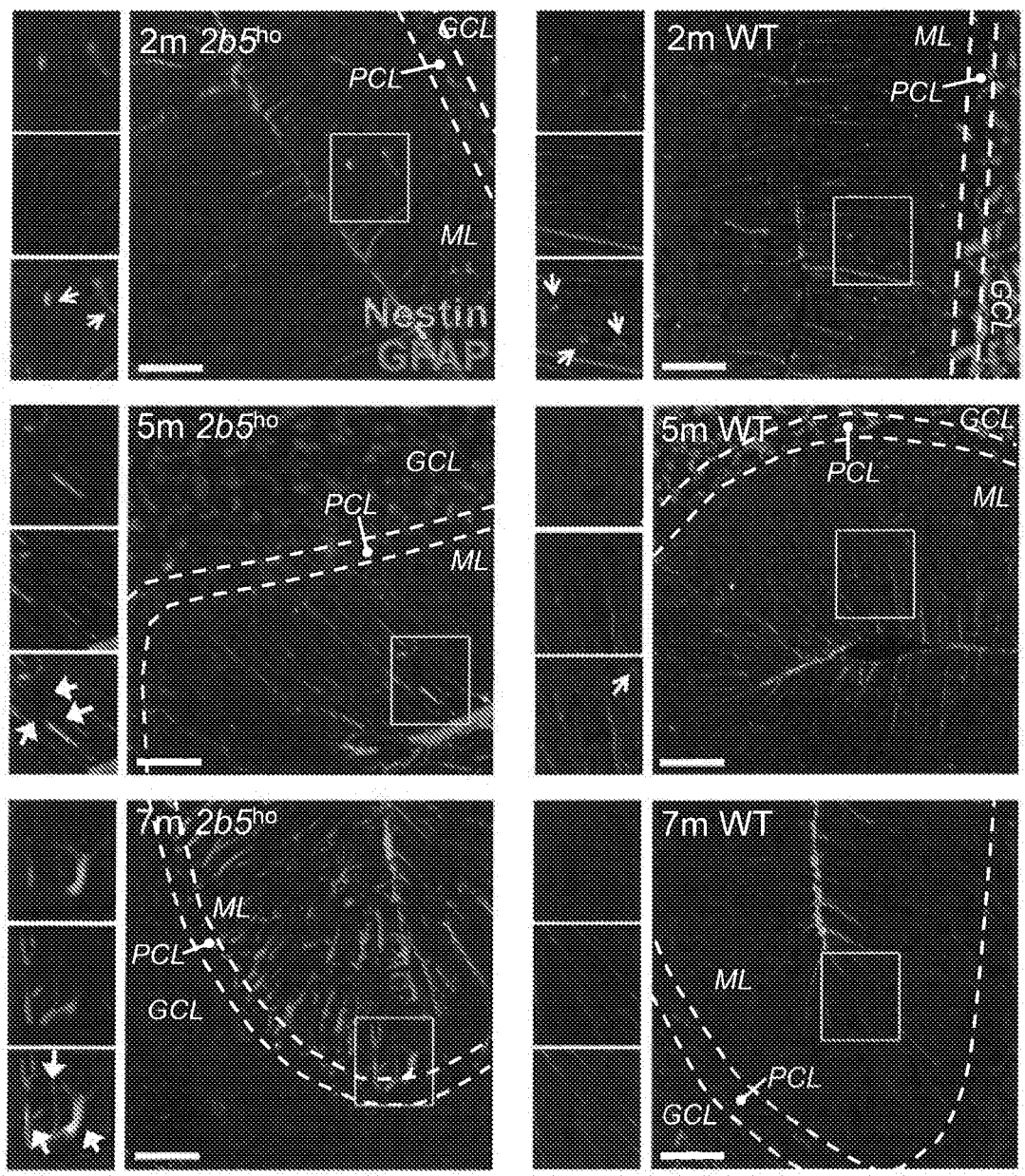

Materials and Methods
Animals
Tissue sections of 11 WT and 10 2b5$^{ho}$ (carrying a homozygous Arg191His mutation in the Eif2b5 gene [7]) animals of 2, 5 or 7 months of age were collected after intracardiac perfusion with 4% paraformaldehyde (PFA). The brains were postfixed in 4% PFA for 1-2 days, after which half of the brain was embedded in paraffin and the other half was incubated overnight in 30% sucrose and snapfrozen in optimum cutting temperature compound (Sakura). The brain of one 3-month-old shiverer mice (kindly provided by Prof. Dr. David Rowitch, UCSF, San Francisco, Calif., USA) was processed in a similar way. To test the effect of Guanabenz, 11 female 2b5$^{ho}$ littermates were injected with saline (n=5) or Guanabenz (10 mg/kg; n=6) i.p. every week from 2 months until 10 months of age. Animals were randomly assigned to the Guanabenz or saline group, and single animals were taken as experimental units. At 11 months of age all mice were sacrificed and the brains were used for analysis. The brains of 3 saline- and 4 Guanabenz-injected animals were perfused as described and used for immunostaining and in situ hybridization. The brains of 2 saline- and 2 Guanabenz-injected animals were snapfrozen in liquid nitrogen and used for western blot analysis. No animals were excluded from any analysis. All animals were weaned at P21 and had ad libitum access to food pellets and water. Mice were considered "symptomatic" when they show motor signs like ataxia, which started around 5 months of age.

Patients
Tissue of 10 genetically proven VWM patients and 4 non-neurologic controls was collected at autopsy. Human tissue was processed as previously described [6]. Patient characteristics including mutations, age at disease onset and age at death are summarized in Table S1. Patients were classified as "mild", "classic" and "severe" based on age of onset and disease duration.

Immunostaining
Mouse tissue was processed for immunostaining as previously described [7]. Shortly, snapfrozen brains were cut in 12 µm thick sections. Sections were pretreated with citrate buffer (pH 6.0) at 90° C. for 10 min. Blocking buffer (phosphate-buffered saline (PBS)+5% normal goat serum+0.3% Triton X-100+0.1% bovine serum albumin) was used for 1 hour blocking and for antibody incubation. See Table 1 for a list of primary antibodies. Secondary antibodies were Goat-anti-mouse Alexa Fluor 488 and Goat-anti-rabbit Alexa Fluor 594. After staining, slides were incubated with 4',6-diamidino-2-fenylindool (DAPI) (Sigma; 1:1000) for 2 min and embedded with Fluoromount G. Human tissue was formalin-fixed, paraffin-embedded and cut in 4 µm thick sections. Sections were deparaffinized and antigen retrieval was performed in Tris/ethylenediaminetetraacetic acid (EDTA) buffer (pH 9) before primary antibody incubation. Immunoreactivity was detected with 3,3'-diaminobenzidine as chromogen and counterstained with hematoxylin. Stainings were analyzed with a LeicaDM6000B microscope (Leica Microsystems). Omitting primary antibodies did not yield any specific staining. Pictures were acquired as TIFF files and optimized for brightness and contrast using Adobe Photoshop 8.0 (Adobe Systems).

Analysis of Bergmann Glia Translocation
Bergmann glia pathology was analyzed in S100ß-stained sections. Per animal 3-6 pictures at 100× magnification of the cerebellar cortex were taken, all including the molecular layer, Purkinje cell layer and granular layer. Analysis was done with Image J software (imagej.nih.gov/ij/); the segmented line tool was used to draw a line through the middle of the Purkinje cell layer. Around this line, a band of 0.406 cm (mouse tissue) or 0.635 cm (human tissue) was made by using the "line to area" and "enlarge" tools (Figure S1). The band sizes were chosen so that the Purkinje cell bodies were completely located inside the band together with the majority of Bergmann glia cell bodies in control tissue. All the S100-positive cell bodies inside this band were counted and considered correctly localized. The S100ß-positive cell bodies located outside the band in the molecular layer were counted and considered as translocated Bergmann glia. The amount of translocated cell bodies was expressed as a ratio to the total number of S100ß-positive cell bodies counted.

Nestin Cell Count

Astrocytes double-positive for nestin and GFAP were counted in the splenium and rostrum of the corpus callosum, on 100× magnification pictures. Total cell number was determined by counting the DAPI-positive nuclei. For each animal, at least 3 slices were stained and counted. The ratio of nestin/DAPI positive cells was used for further analysis.

Analysis of Purkinje Cell Number

The number of Purkinje cells in the cerebellum was assessed with staining for Calbindin on 100× magnification pictures. For each animal, at least 6 pictures of different areas of the cerebellum were taken, all including the Purkinje cell layer. The number of Purkinje cells in each picture was counted and corrected for the length of the Purkinje cell layer, which was measured by drawing a line through the Purkinje cell layer using the "segmented line" tool in ImageJ and measuring the length of the line with the "Measure" option.

In Situ Hybridization

In situ hybridization targeting proteolipid protein (Plp) mRNA was performed on PFA-fixed snapfrozen tissue as previously described [7, 25]. Plp probe was incubated overnight in hybridization buffer, targeted with anti-digoxygenin (1:2000, Roche) and developed with BM purple (Roche). Nuclei were counterstained with 0.5% methylgreen. The number of Plp-positive cells was analyzed in the rostrum and splenium of the corpus callosum, and in the white matter of the cerebellum. For each area 3 different pictures were taken with a 100× objective lens and cells were counted in a 100×200 µm square.

Western Blot

Half of the forebrain and the whole cerebellum of 2 saline- and 2 Guanabenz-treated animals were separately used for western blot analysis. Forebrains were lysed in lysis buffer (50 mM Hepes, 150 mM NaCl, 1 mM EDTA, 2.5 mM ethylene glycol-bis(β-aminoethyl-ether)-N,N,N',N'-tetraacetic acid, 0.1% Triton-X100, 10% glycerol, 1 mM dithiothreitol) supplemented with protease inhibitor cocktail (ThermoFisher Scientific) using a dounce tissue grinder (Sigma-Aldrich). Samples were incubated on ice for 20 min and centrifuged 15 min at 13.000 rpm. Supernatants were collected and protein concentrations were measured with a Bradford assay. Samples (60 µgr of total protein) were separated on a 12% SDS-PAGE gel and transferred onto an activated polyvinylidene fluoride-membrane. After the transfer blots were scanned on a BioRad scanner to measure total protein content (Figure S2). Blots are blocked for 1 hour with 5% milk in PBS and incubated overnight in primary antibody diluted in 2.5% milk in PBS at 4° C. The next day, blots were blocked for 10 min in 5% milk and incubated in secondary antibody diluted in 2.5% milk in PBS at room temperature for 1 hour. Secondary antibodies were raised against mouse or rabbit and conjugated with horseradish peroxidase. Blots were developed with Super-Signal™ West Femto Maximum Sensitivity Substrate (ThermoFisher Scientific) and measured in an Odyssey® Fc Imaging System (LI-COR Inc). Intensity of bands was quantified with ImageJ software and corrected for total amount of protein. Total protein content as a loading control is more sensitive than a single-protein loading control and less susceptible for variation due to treatment [26, 27].

Statistical Analyses

Data of nestin cell counts, Bergmann glia localization and Plp cell counts was analyzed with SPSS software package (IBM SPSS Statistics 20.0). Data was analyzed with an independent samples t-test if the data met the assumptions for a parametric test and if the distribution did not deviate significantly from normal as determined by a Shapiro-Wilk test. For data that did not meet parametric assumptions a Mann-Whitney U test was performed. For trend analysis a one-way ANOVA with polynomial contrasts was used. Pearson's correlation coefficient r was used as a measure for the effect size ($r>0.5$ was considered a large effect) and to analyze the correlation between different variables.

Results

Bergmann Glia in Late Symptomatic VWM Mice Express Radial Glia Marker RC2 and Neural Stem Cell Marker Nestin Astrocytes in postmortem tissue of VWM patients and in the forebrain of adult $2b5^{ho}$ mice express markers of immaturity [7]. In the corpus callosum, astroytic abnormalities can already be observed in the first postnatal weeks in the $2b5^{ho}$ mice, while clinical symptoms as ataxia only appear from 5 months of age onwards. So far it is unclear whether the Bergmann glia show other markers of immaturity besides GFAPδ and at what age these become apparent. Therefore we performed immunohistochemistry for the radial glia marker RC2 and neural stem cell marker nestin at the postmortem cerebellum of $2b5^{ho}$ mice of different ages. The RC2 antibody recognizes a variant of Nestin that is under normal circumstances only expressed in radial glial. Bergmann glia in 7-month-old $2b5^{ho}$ animals showed immunopositivity for RC2, which was undetectable in adult age-matched WT mice and in 2- and 5-month-old $2b5^{ho}$ animals (FIG. 1A). RC2 staining was present in Bergmann glia that were mostly also bright GFAP-positive, had a translocated soma into the molecular layer and showed an abnormal morphology with short, thick processes that were retracted from the pial membrane (FIG. 1A). Nestin expression was present in Bergmann glia of 5- and 7-month-old $2b5^{ho}$ animals, but not in 2-month-old $2b5^{ho}$ animals and WT animals of any age (FIG. 1B). The expression of nestin was more prominent in Bergmann glia with an abnormal morphology, that were previously shown to have an increased expression of GFAPδ at similar ages.

Alongside immaturity, the proliferation status of Bergmann glia was determined. CyclinD1 is a protein that is abundant in the G1 and the G1/S phase transition during the cell cycle, and therefore labels proliferating cells. Staining of 7-month-old $2b5^{ho}$ and WT animals with CyclinD1 and GFAP showed that the translocated Bergmann glia with abnormal morphology were not CyclinD1 positive (Figure S3A). So Bergmann glia in 7-month-old $2b5^{ho}$ mice express markers of immaturity but do not express the proliferative cell marker Cyclin D1 at 7 months of age. Immunocytochemistry for Calbindin in 7-month-old $2b5^{ho}$ and WT animals showed no abnormalities in amounts or morphology of Purkinje cells in the $2b5^{ho}$ mice ([7]; Figure S3B-C).

Bergmann Glia Translocation is a Quantitative Measure of VWM Pathology

Figure 2:
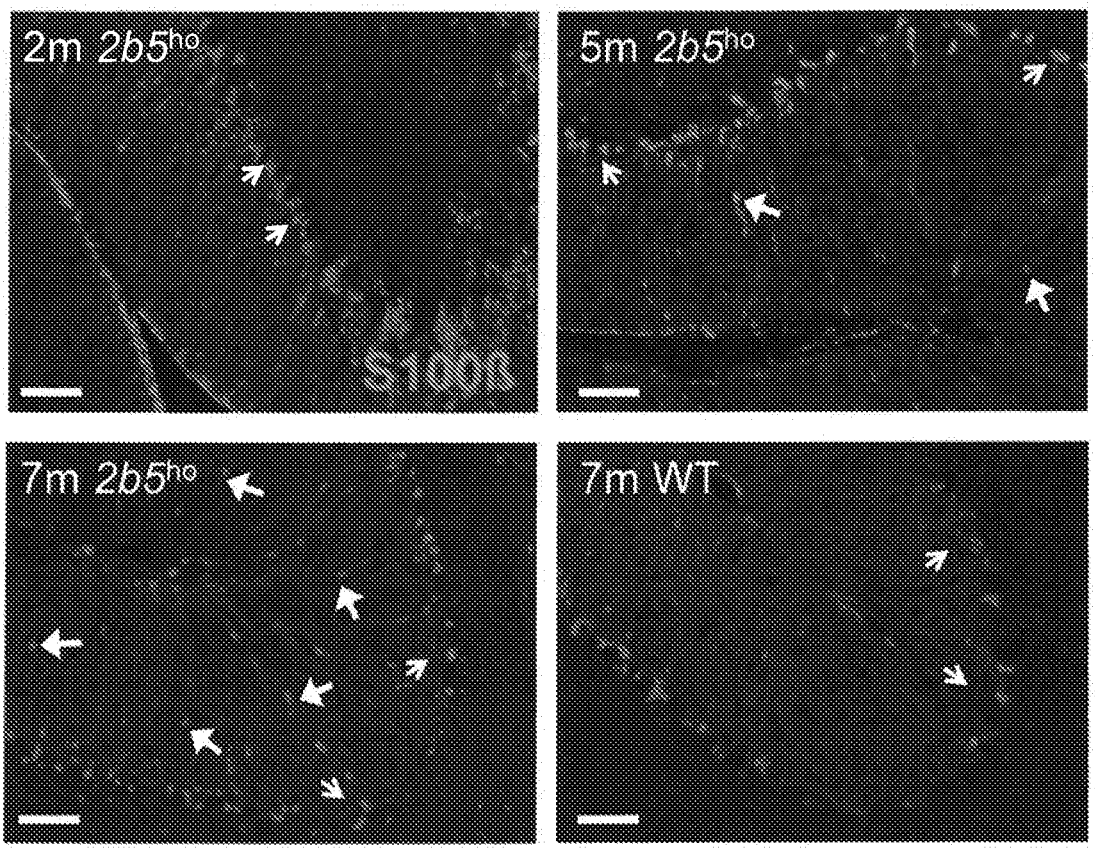
FIG. 2. Bergmann glia translocate into the molecular layer in VWM mice. (A) Immunostaining for S100ß shows Bergmann glia cell bodies and processes in 7-month-old WT and 2-, 5- and 7-month-old $2b5^{ho}$ mice. In WT mice the majority of the Bergmann glia cell bodies is located in the Purkinje cell layer (see arrows). Bergmann glia in the 5- and 7-month-old $2b5^{ho}$ mice have cell bodies translocated to the molecular layer (Large arrows; normally localized cell bodies are indicated by small arrows). (B) Data points show the ratio between S100ß-positive cell bodies in the molecular layer and the total number of S100ß-positive cell bodies. Each data point represents an individual mice, with solid data points indicating mean±SEM. *=$p<0.05$; **=$p<0.01$. Scale bar=50 μm; BG=Bergmann glia.
Figure 2:
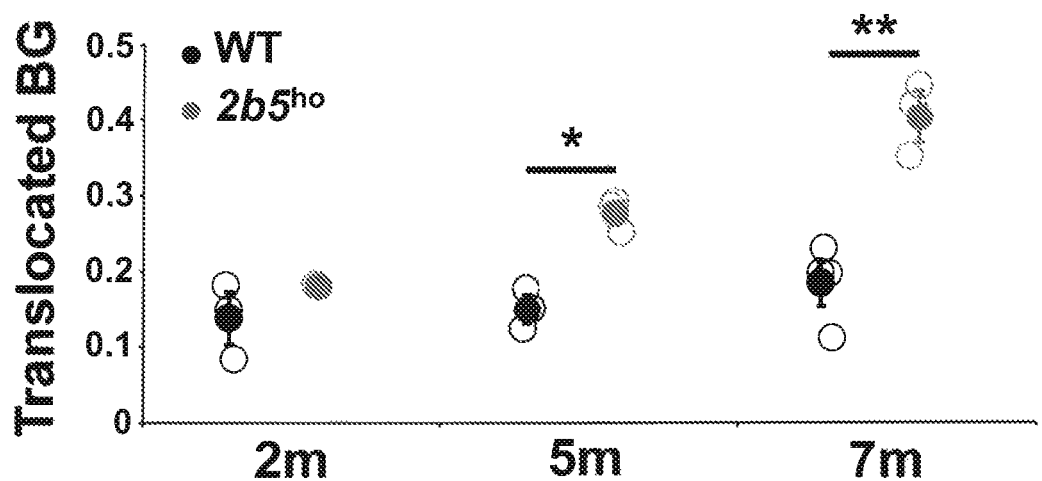

While in normal conditions the nuclei of Bergmann glia are located in the Purkinje cell layer, symptomatic VWM mice and patients show translocation of Bergmann glia nuclei to the molecular layer, worse so in mice with more severe disease [7]. To use Bergmann glia translocation as a biological read-out for treatment effectiveness, we developed a method that allowed quantitative assessment of Bergmann glia pathology. Cryo-preserved sections of 2-, 5- and 7-month-old WT and 2b5$^{ho}$ mice were immunostained for S100ß, which visualizes both soma and processes of Bergmann glia. The number of S100ß-positive cell bodies inside and outside the Purkinje cell layer was counted. At 5 months (p=0.046) and 7 months (p=0.002) of age, 2b5$^{ho}$ mice showed a significantly increased number of translocated Bergmann glial cell bodies (FIG. 2A-B, Table S2). The linear trend of the Bergmann glia translocation from 2-month-old to 7-month-old 2b5$^{ho}$ mice was significant (p=0.001, r=0.94), indicating that Bergmann glia translocation becomes apparent at symptomatic disease stages of VWM and worsens over the disease course.

Figure 3:
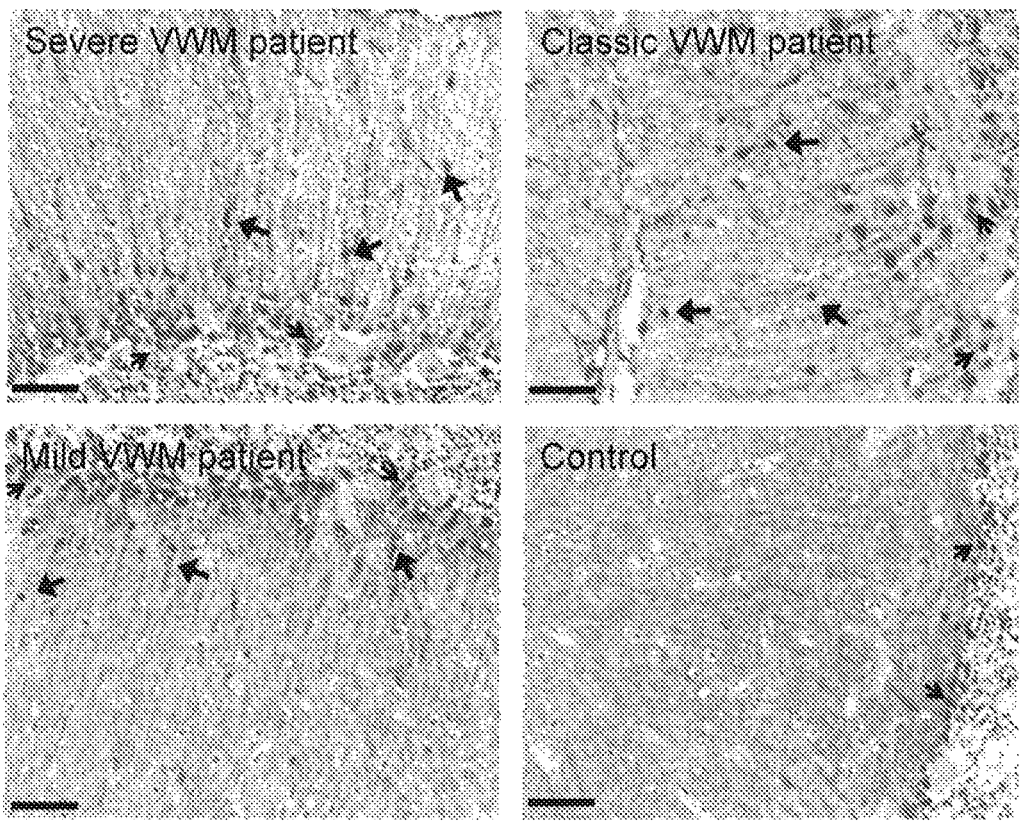
FIG. 3. All VWM patients with different disease severities show Bergmann glia translocation. (A-B) Immunostaining for S100 shows a significantly higher number of translocated Bergmann glia in tissue of VWM patients with severe, classic and mild forms than in control tissue. Large arrows indicate translocated Bergmann glia; normally localized cell bodies are indicated by small arrows. (C) A linear trend line shows a negative correlation with age for VWM patients, although the trend is not significant. (B) Each data point represents an individual patient or control, with solid data points indicating mean±SEM. (C) Each data point represents an individual patient or control, with a linear trend line showing the correlation between age and Bergmann glia translocation. **=$p<0.01$. Scale bar=50 μm. Ctrl=Control, BG=Bergmann glia FIG. 4. Guanabenz treatment improves Bergmann glia pathology. (A-B) The number of nestin-GFAP double positive cells is decreased in the corpus callosum of 3 out of 4 Guanabenz-treated animals compared to saline-treated animals. (C-D) The number of translocated Bergmann glia nuclei is significantly decreased after Guanabenz treatment. GFAP staining also shows a normalization of the Bergmann glia morphology in Guanabenz treated animals (see inset). (A,C) Data points represent individual mice, with solid data points indicating mean±SEM. animals. Scalebar=50 μm; *=$p<0.05$. BG=Bergmann glia, GBZ=Guanabenz.
Figure 3:
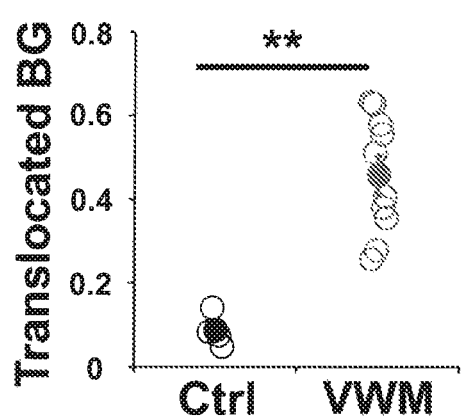
Figure 3:
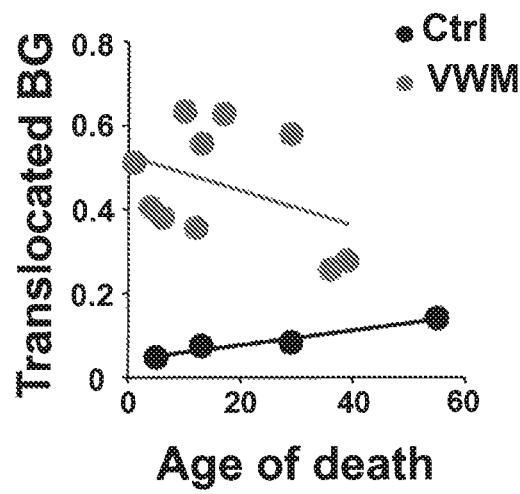

Analysis of brain tissue of 10 VWM patients with different disease severities showed that all patients have increased Bergmann glia translocation compared to controls (FIG. 3A-B, Table S2). Between patients there was quite some variance in the number of translocated Bergmann glia, and a trend towards a lower number of translocated Bergmann glia in the older (milder) VWM patients was observed (FIG. 3C), although non-significant. As no Bergmann glia translocation was observed in the brain of the shiverer mouse (Table S2), this disease marker is not a general feature of brain white matter abnormalities.

Guanabenz Treatment Rescues Bergmann Glia Translocation

Figure 4:
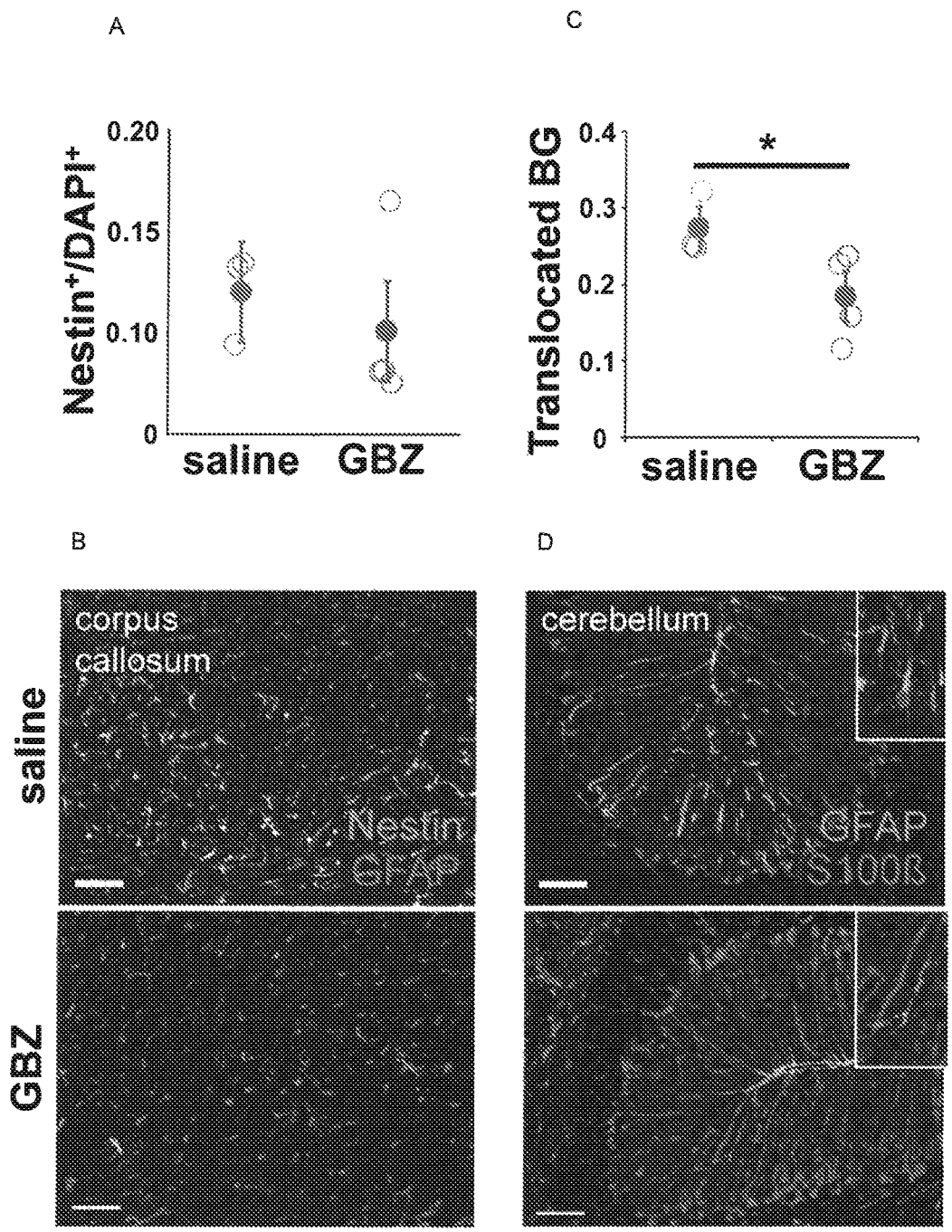

To analyze whether Guanabenz treatment improves VWM pathology, 2b5$^{ho}$ mice were treated with 10 mg/ml i.p. Guanabenz between 2- and 10 months of age. At 11 months of age, Guanabenz- and saline-treated animals were sacrificed and first analyzed for the pre-symptomatic disease marker nestin. The number of nestin-positive cells in the corpus callosum decreased in all but one Guanabenz-treated animal compared to saline-treated animals (FIG. 4A-B, Table S3), but the average decrease of 27% failed to reach significance (p=0.289). To test whether Guanabenz treatment rescues biomarkers of the symptomatic disease state, we analyzed Bergman glia cell localization. We found that the Guanabenz treatment significantly decreased the number of translocated Bergmann glia cell bodies by 30% and reached the numbers found in untreated WT animals. (p=0.032; FIG. 4C-D, Table S2). This was accompanied by a decreased GFAP expression and a normalization of Bergmann glia morphology (FIG. 4D). These data indicate that Guanabenz treatment improves VWM pathology, and rescues Bergman glia translocation when started at early-symptomatic disease stages.

Guanabenz Treatment Improves Myelin Pathology in the Cerebellum of VWM Mice

Figure 5:
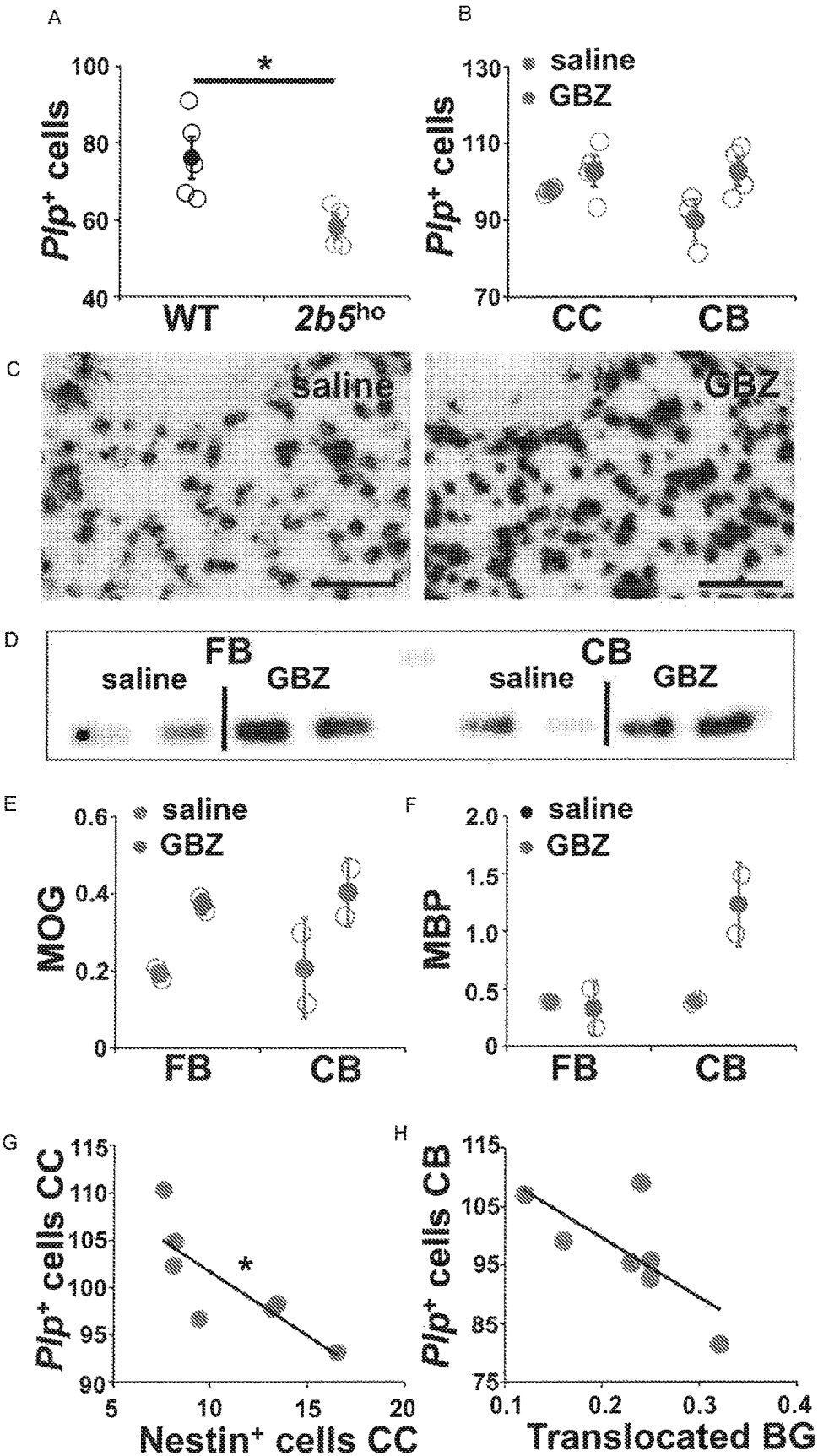
FIG. 5. Oligodendrocyte and myelin pathology is improved in the cerebellum after Guanabenz treatment. (A) The number of Plp-expressing cells in the cerebellum of $2b5^{ho}$ mice is significantly lower than in the cerebellum of WT mice. After Guanabenz treatment an increase in the number of Plp-expressing cells is observed in both the corpus callosum (B) and in the cerebellum (B-C), but not significantly. (D-E) Western blot analysis of protein lysates shows increased amounts of MOG protein in the forebrain and cerebellum of Guanabenz treated animals compared to saline-treated animals. (F) The amount of MBP protein is increased in the cerebellum but not in the forebrain of Guanabenz treated animals. Correlation analysis shows a significant inverse correlation between the number of nestin-positive and Plp-positive cells in the corpus callosum (G), but the correlation between translocated Bergmann glia and the Plp-positive cells in the cerebellum does not reach the level of significance (H). (A-B; E-F) Data points represent individual mice, with solid data point indicating mean±SEM. (G-H) Data points represent individual mice, with a linear trendline showing the correlation between variables. *=p<0.05. CC=corpus callosum, CB=Cerebellum, FB=forebrain, GBZ=Guanabenz.
Figure 6:
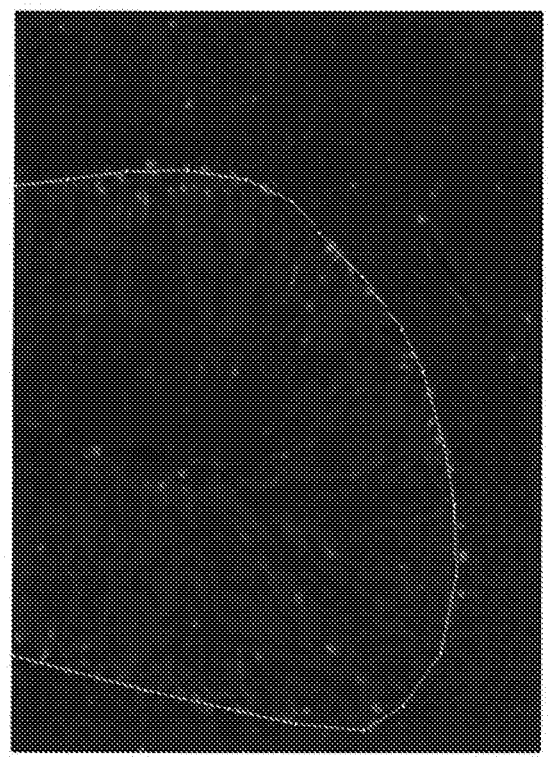
FIG. 6. Quantification of Bergmann glia cell body translocation. Bergmann glia translocation is quantified on 100× magnification pictures of S100ß staining. Images are opened in Image J, and with the segmented line tool an line through the Purkinje cell layer is drawn (A). With the "line to area" and "enlarge" tool, the line is expanded to a band of 0.406 cm (mice) or 0.635 cm (human) (B). The S100ß-positive nuclei inside the band are considered correctly localized, and the S100ß-positive nuclei in the molecular layer outside the band are considered translocalized (C). (D) shows an example of the 0.635 cm band on a picture of a human tissue section stained with S100.
Figure 6:
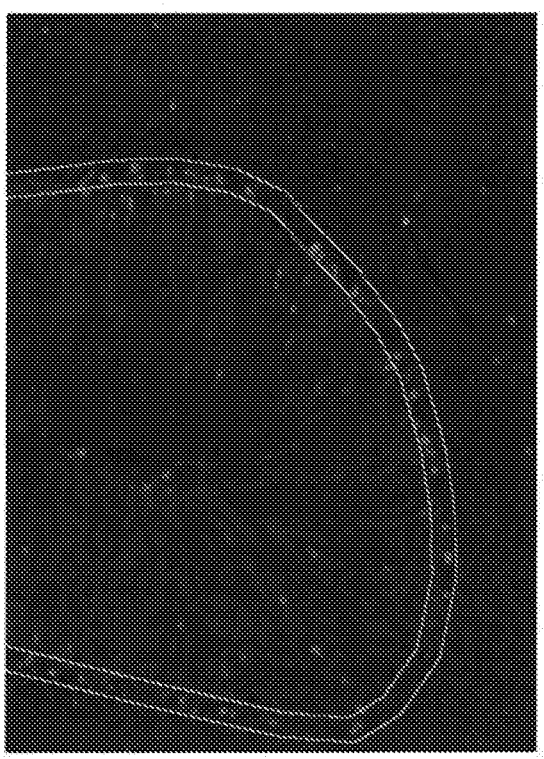
Figure 6:
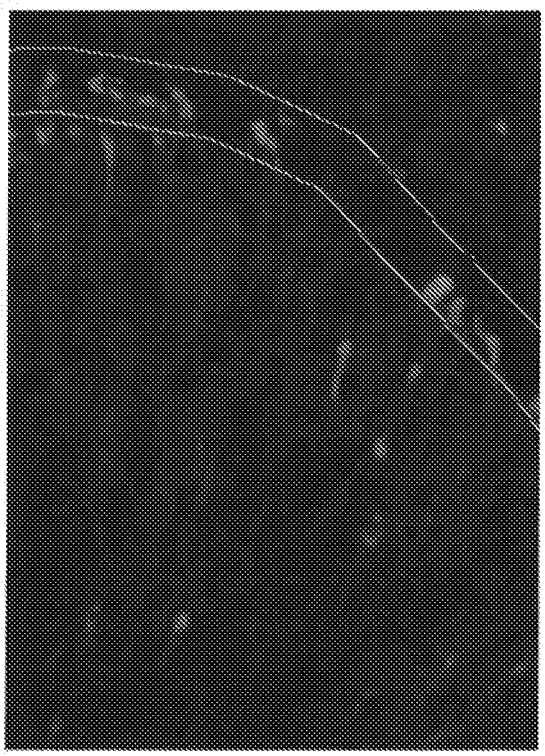
Figure 6:
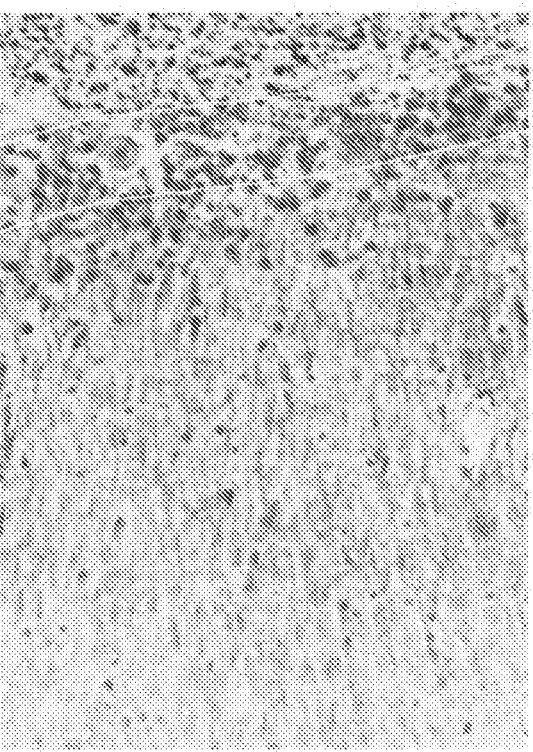
Figure 7:
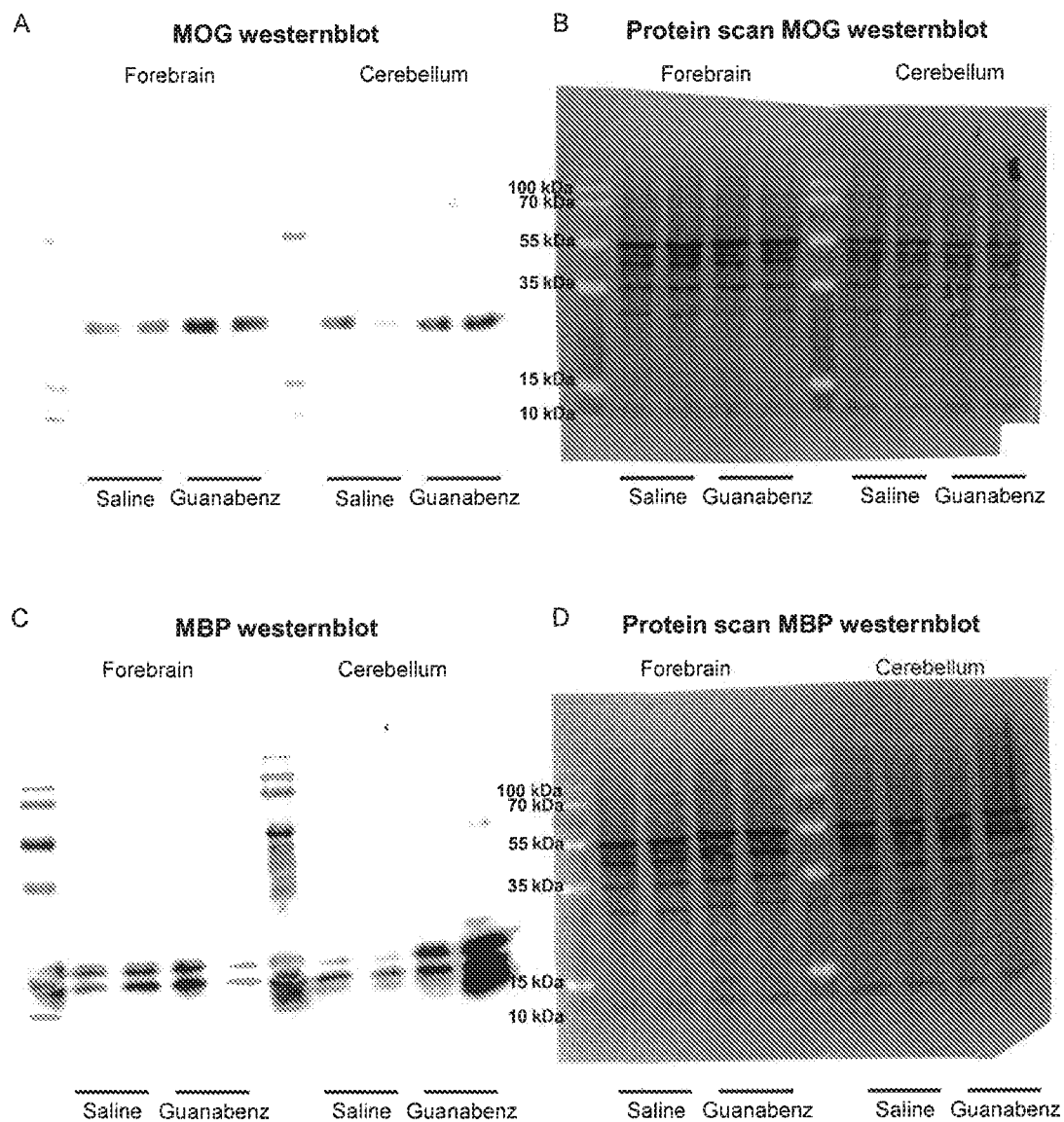
FIG. 7. Original western blots. (A) Complete western blot probed with MOG antibody, (B) shows the protein scan of the same blot used for quantification. (C) Complete western blot probed with MBP antibody, (D) shows the protein scan of the same blot used for quantification.
Figure 8:
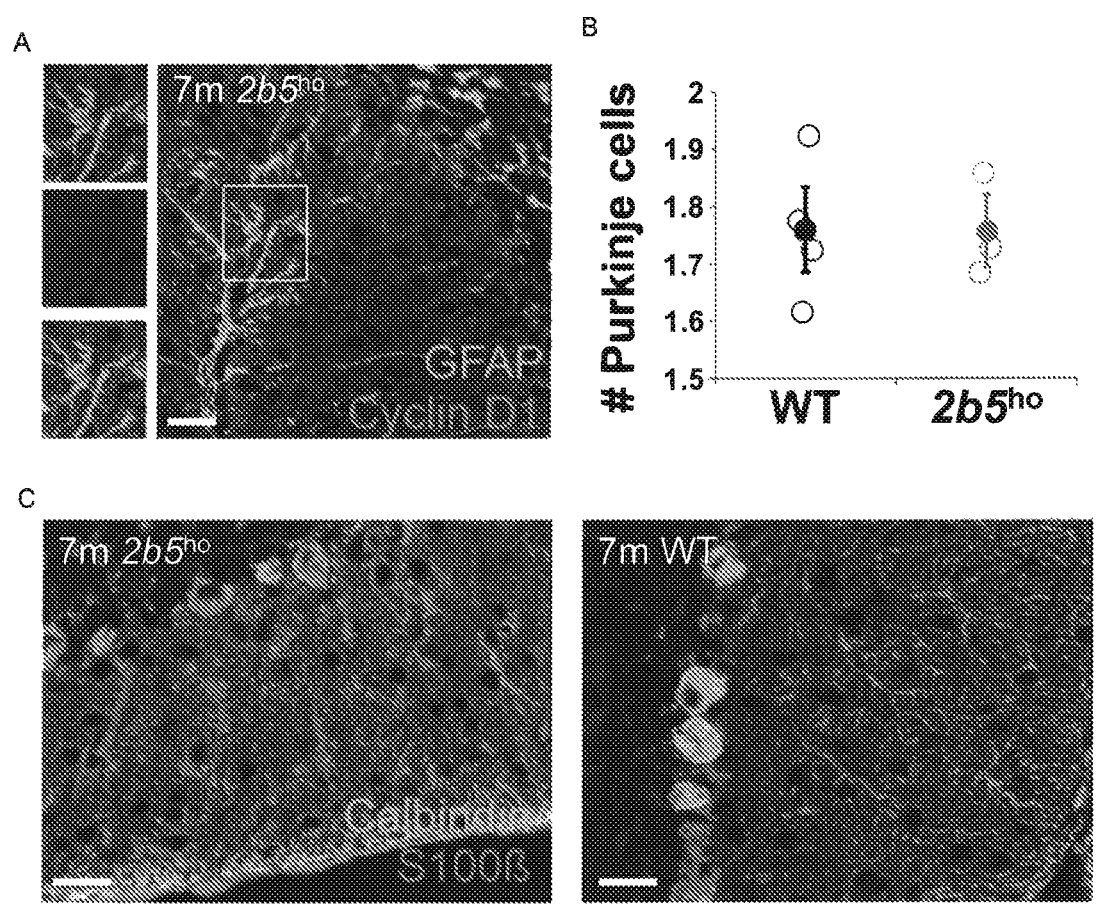
FIG. 8. Purkinje cells do not show abnormalities in VWM. Staining for Cyclin D1 shows that Bergmann glia with an abnormal morphology are not Cyclin D1 positive (A) suggesting that they are not proliferating. The amount of Purkinje cells (B) is similar in 7-month-old WT and 2b5ho mice, and staining for Calbindin shows no abnormalities in Purkinje cells of 2b5ho mice (C). (B) Data points represent individual mice, with solid data points indicating mean±SEM. animals. Scalebar=25 µm.

The 2b5$^{ho}$ mice show oligodendrocyte abnormalities and myelin pathology [7], which was previously quantified in the corpus callosum with in situ hybridization for Plp, a marker for mature oligodendrocytes. To validate myelin abnormalities in the cerebellum, we now analyzed Plp expression in the cerebellar white matter of 7-month-old 2b5$^{ho}$ and WT mice. The number of Plp-expressing cells in the cerebellum of 2b5$^{ho}$ mice was significantly lower than in the cerebellum of WT mice (FIG. 5A, Table S4). After Guanabenz treatment, the number of Plp-expressing cells was slightly increased in the forebrain and cerebellum, though not significantly (FIG. 5B-C, Table S4). The increase was higher in the cerebellum than in the corpus callosum.

To analyze the effects of Guanabenz treatment on myelin pathology in the cerebellum of 2b5$^{ho}$ animals, we performed Western blot analysis for the mature myelin proteins myelin basic protein (MBP) and myelin-oligodendrocyte glycoprotein (MOG). Both were increased in the cerebellum of 2b5$^{ho}$ animals after Guanabenz treatment (FIG. 5D-F, Table S5, Figure S2). In the forebrain only the amount of MOG protein was increased. So Guanabenz-treated 2b5$^{ho}$ animals showed improvement of oligodendrocyte and myelin pathology, which was more prominent in the cerebellum than in the forebrain.

Markers of Astrocyte and Oligodendrocyte Pathology in Different Brain Regions Correlate with Disease Severity in Different Temporal Patterns Interestingly, the Guanabenz-treated animal that showed the highest number of nestin-positive cells also showed the lowest number of Plp-expressing cells in the corpus callosum. This finding prompted a correlation analysis between the different markers. In the corpus callosum, we confirmed a significant inverse correlation between the number of nestin-positive cells and the Plp-positive cells (r=−0.811, p=0.027, FIG. 5G, Table S6). In the cerebellum, we found an inverse correlation between the number of Plp-positive cells in the cerebellar white matter and the ratio of translocated Bergmann glia, but this correlation was not significant (r=−0.723, p=0.66; FIG. 5H, Table S6). We looked at the correlations between measurements in different brain areas and found no significant correlation between measures for the corpus callosum and the cerebellum (Table S6). So the measurements of different brain areas, which all correlate with disease severity, lack significant correlations between each other suggesting some degree of independence between the pathology in those areas.

Discussion

Different astrocytic cell populations are affected in the brain of VWM patients, which is recapitulated in recently developed VWM mouse models. Cerebellar Bergmann glia in both VWM patients and symptomatic mice show upregulated expression of GFAPδ and lost radial morphology. One of the clearest signs of VWM pathology in the cerebellum is translocation of Bergmann glia into the molecular layer [7]. In the current experiments we used the 2b5$^{ho}$ VWM mouse model to determine Bergmann glia pathology in more detail.

Bergmann glia have important functions in the development of cerebellar cortical architecture and in information processing in the molecular layer of the adult cerebellar cortex [28]. Our analysis of the Bergmann glia showed that staining for the radial glia marker RC2 is present in symptomatic VWM mice. Since RC2 immunopositivity is normally not present in the adult brain [29], these results indicate that Bergman glia like other glia cell populations in the VWM brain have an immature phenotype. While Bergmann glia are important for proper layering in the cerebellum, we found no changes in the cerebellar architecture of the cortical cell layers [7]. Quantification of Bergmann glia translocation at different disease states showed that the number of translocated Bergmann glia is significantly increased at 5 and 7 months of age compared to control mice, when VWM mice start to show clinical symptoms. In younger animals Bergmann glia have normal localization and morphology and do not express early markers like nestin and RC2. By contrast, white matter astrocytes in the corpus callosum of VWM already show nestin overexpression at P14 [7]. In VWM patient tissue only the disease end-stage can be assessed, and it is not possible to track the Bergmann glia translocation within one patient over time. All patients showed Bergmann glia translocation. VWM disease severity and age of onset (and death) are inversely correlated. In the oldest VWM patients, with a mild disease variant, the number of translocated Bergmann glia was lower than in the younger patients. This suggests a correlation between disease severity and Bergmann glia translocation, although this needs to be confirmed in a larger group of patients. Abnormalities of Bergmann glia translocation were not observed in the myelin deficient shiverer mice, which lacks astrocytic abnormalities. This suggests that Bergmann glia translocation is not a general consequence of white matter abnormalities.

Why Bergmann glia in VWM translocate into the molecular layer is not known. Since Bergmann glia have tight connections with Purkinje cells [28], this phenomenon could be linked to Purkinje cell pathology. However, no loss of Purkinje cells is observed in VWM mice. Upregulation of Nestin and GFAP in Bergmann glia is further seen upon e.g. traumatic injury [30, 31] and in Creutzfeldt-Jacobs disease [32]. While upregulation of Nestin and GFAP is a known feature of reactive astrocytes, reactive Bergmann glia do not form a glial scar like other astrocytes. Additionally, they keep their normal position and, when Bergmann glia processes are damaged, their radial glia like morphology is recovered over time. Therefore, the Bergmann glia translocation observed in VWM does not correspond to "normal" reactive gliosis of Bergmann glia. So, other mechanisms must underlie Bergmann glia translocation in VWM. Maturation and fiber formation of Bergmann glia is tightly regulated during development and requires active maintenance later in life [28]. For proper functioning of the Bergmann glia, their processes need correct anchoring to the basement membrane on the cerebellar surface. Dysregulation of proteins and pathways involved in these assembles, like ß1-integrin, α-dystroglycan, Notch, FGF9 and the P13K/AKT pathway (see [28] for extensive review), will lead to loss of Bergmann glia morphology, translocation of Bergmann glia cell bodies to the molecular layer and consequently disrupted cerebellar layering. Glia-specific knockdown of components of the Notch [33] and Wnt [34] signaling pathways can lead to abnormal Bergmann glia morphology and localization in later postnatal stages, without effecting cerebellar layering. Interestingly, mice with a knockdown of adenomatous polyposis coli in GFAP-expressing cells show Bergmann glia translocation to the molecular layer like VWM mice [34]. Further research is needed whether one of these mechanisms is involved in the translocation of Bergmann glia in VWM.

Astrocyte dysfunction is thought to underlie the myelin deficits found in VWM. Here we show that Guanabenz treatment rescues Bergmann glia translocation in VWM mice. Interestingly cerebella of the Guanabenz-treated VWM mice also showed improvements in myelin content. In the corpus callosum the astrocyte pathology was not significantly improved with Guanabenz treatment, and the increase in number of mature oligodendrocytes and myelin content was smaller than in the cerebellum.

To address effectiveness of treatment options, disease markers that fit the treatment window should be evaluated. An increased number of nestin-positive astrocytes in the corpus callosum of VWM mice is already observed at P14, during pre-symptomatic disease stages. Since Guanabenz injections were only started at 2 months of age, it is likely that Guanabenz treatment was initiated too late to rescue disease makers of pre-symptomatic disease stages. Indeed, the numbers of Nestin-positive cells in the corpus callosum were not significantly reduced, although 3 out of 4 Guanabenz treated animals showed a decreased number. Although increased nestin cell counts in the corpus callosum reliably marks VWM from the pre-symptomatic stage onwards, its sensitivity to treatment needs further tests to validate it as a VWM disease marker sensitive to therapy. By contrast, Bergmann glia abnormalities are only observed from 5 months of age onwards, increase with disease progression and clearly improve with treatment. As the Bergmann glia abnormalities start at the same time as clinical signs like ataxia, Bergmann glia translocation cannot be used as a predictive marker for VWM in pre-symptomatic disease stages. However, it is sensitive for treatment and can therefore be used in studies testing new treatment options. There was a significant inverse correlation between the number of nestin-positive astrocytes and the number of Plp-positive oligodendrocytes in the corpus callosum of $2b5^{ho}$ mice. This suggests that decreased astrocyte dysfunction correlates with improved myelin in the corpus callosum, either through a causative relation or by an underlying mechanism affecting both astroytes and oligodendrocytes equally. Absence of direct contact between Bergmann glia in the Purkinje cell layer and the Plp-positive oligodendrocytes in the white matter of the cerebellum could explain the less strong correlation between these populations. We found no significant correlation between measurements of the cerebellum and the corpus callosum. So different parameters of VWM pathology are only correlated within the same brain region. All individual markers reliably predict and correlate with the disease state, but in a different temporal pattern. This suggests that the measurements in the different regions are independent from each other, while all correlate with disease severity. Therefore using all three measures together gives a more complete picture of different aspects of VWM pathology.

Guanabenz-treated animals only showed significant improvements for some parameters, which is possibly explained by the choice of dose and timing of administration. A dose of 4-16 mg/kg Guanabenz is sufficient to achieve brain levels capable of modulating the endoplasmic reticulum stress response [19]. However daily injections are more effective than weekly injections [15], possibly because the effect of Guanabenz on p-eIF2 is only short-lived [19]. Taking these studies into account, increased improvements using daily administration of a lower dose of Guanabenz are expected. Additionally, other compounds that regulate eIF2 phosphorylation should be tested, as Guanabenz acts as a2 adrenergic receptor agonist mainly. For example, Das et al. [35] recently have synthesized Sephin1, which lacks a2-adrenergic activity, but sustains p-eIF2 under ER stress conditions and is able to cross the blood-brain-barrier. Sephin1 treatment improved the phenotype of mice modeling Charcot-Marie-Tooth disease and amyotrophic lateral sclerosis. No adverse side effects after acute or chronic treatment of Sephin1 in mice were observed. The Guanabenz treatment regimen used in the present invention shows improved treatment protocols are possible with Guanabenz itself or other compounds that can regulate eIF2 phosphorylation.

To conclude, we show that Bergmann glia translocation is a quantifiable disease marker for symptomatic disease stages of VWM and provides a sensitive measure for disease progression and treatment effectiveness that can be used in mice. Although the Guanabenz treatment regimen chosen only gave significant improvements for some parameters of VWM pathology, the present invention shows that compounds acting on p-eIF2 have good prospects for future treatment strategies for VWM, involving a more intensive treatment schedule or a multimodal treatment approach together with e.g. cell or gene therapy. We are currently preparing a clinical trial to assess the effects of Guanabenz on disease progression in VWM patients.

Example 2

Cellular stresses increase the level of phosphorylated eIF2a, which sequesters eIF2B in an inactive form. This pathway is known as the integrated stress response (ISR). As a consequence of decreased eIF2B activity, the overall protein synthesis rate is inhibited, but increased for specific mRNAs. The mRNA encoding ATF4 is such an mRNA: the synthesis of the ATF4 protein increases during the ISR. ATF4 is a transcription factor that induces expression of various genes that are important for protective cellular responses and for negative feedback regulation. ATF4-regulated genes include DDIT3 (encoding CHOP), TRIB3 and GADD34. As a consequence of this combined expression, cells can cope with and counteract cell stress and return to their normal state when the stress has been relieved, or die if the stress was too longstanding or severe. VWM is caused by mutations in eIF2B subunits, decreasing its activity. Consequently, ATF4 and its transcriptome are always activated.

The a2 adrenergic receptor agonist Guanabenz (Gb) has been reported to also target GADD34 and thereby impact on a negative feedback loop of the ISR [16]. GADD34 promotes dephosphorylation of eIF2P. Gb is thought to inhibit GADD34, it is thereby though to increase and prolong eIF2a phosphorylation and consequently increases production of ATF4 and its regulated transcriptome. We tested the effect of Gb on ATF4 production in U373 cell lines using a stress-sensitive transfection assay. Transfections were performed with the pNL1.1-mATF4 reporter construct, in which expression of the reporter gene is controlled by ISR-responsive sequences. Expression from the reporter construct was measured 2 days after transfection with a commercially available chemiluminescent assay [36] and can be directly interpreted as a measure for ATF4 expression.

Figure 9:
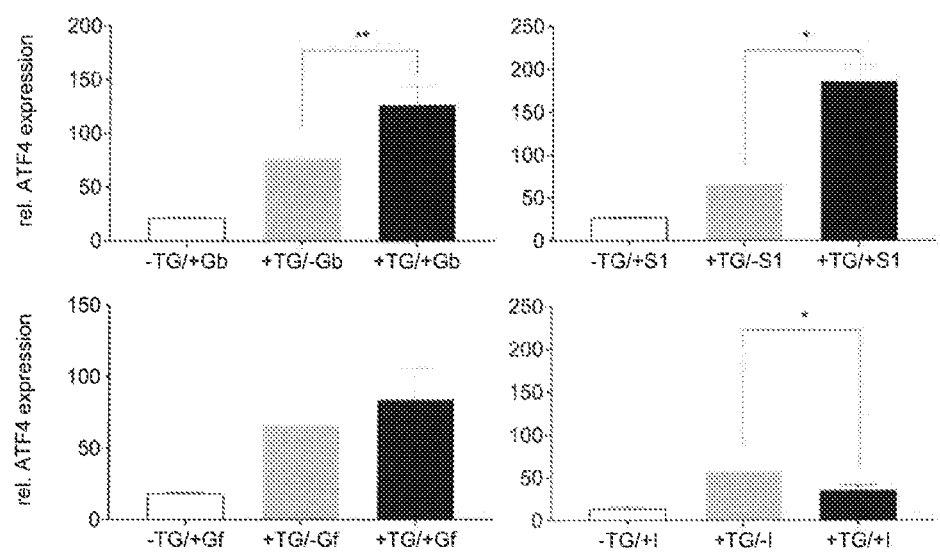
FIG. 9. Stress-induced ATF4 expression is significantly increased by Guanabenz (Gb) and Sephin1 (S1) in human astroglioma cell line (U373). ATF4 expression was assessed with a luciferase reporter construct under regulation of the murine Atf4 promoter and 5' non-coding region. Cells were transfected as described [36]. The ISR was induced by administration of 3 nM thapsigargin (TG) to the cell culture medium. 15 µM ISR modulators Gb, Sephin1 (S1, also a GADD34 inhibitor, but without α2 adrenergic effect) or ISRIB (I, an activator of eIF2B) were added simultaneously with or without TG for 16 hours (e.g. −TG/+Gb and +TG/+Gb). Guanfacin (Gf), an α2 adrenergic receptor agonist without reported GADD34 modulating activity, was included in parallel as negative control. Cell stress modulators Gb and S1 increase ATF4 expression in the presence of TG. This effect was not observed with Gf and was opposite in ISRIB. Statistical analyses were performed for individual compounds with a paired t-test (*, p<0.05, **, p<0.01).

ATF4 expression was investigated in the absence or presence of ISR activation. The ISR was induced by addition of thapsigargin to the culture medium 16 hours before cells were harvested and ATF4 synthesis was measured. Gb was added together with thapsigargin to the culture medium to test the effect of Gb on ATF4 expression. In this experiment we included additional compounds as controls in parallel cultures: Sephin1 (another compound with GADD34-inhibiting capacity but without a2 adrenergic receptor agonism) and Guanfacine (an a2 adrenergic receptor agonist without GADD34 inhibiting capacity). The eIF2B-enhancing compound ISRIB was included as positive control for ATF4-regulation. This compound reduces ATF4 expression [37; 38]. The results are shown in FIG. 9. The compounds behaved as expected: Gb and Sephin1 increased and ISRIB reduced ATF4 expression under stress. The effect of Guanfacine on ATF4 expression was small, variable and not statistically significant. Sephin1 seemed to increase ATF4 expression more effectively than Gb, but the effect did not reach statistical significance.

Figure 10:
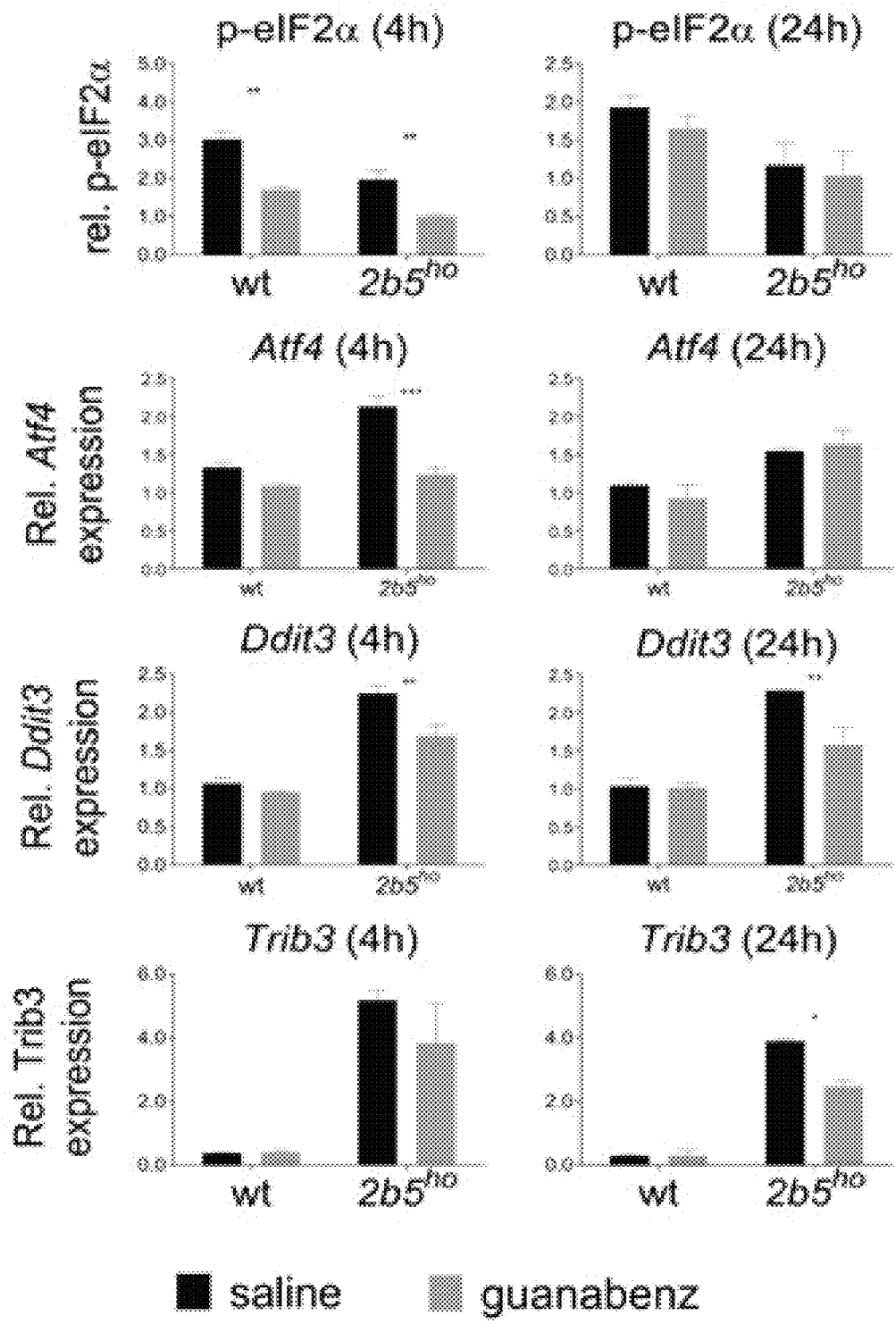
FIG. 10. Guanabenz transiently reduces eIF2a phosphorylation in brain tissue from control and 2b5ho mutant mice, which is accompanied by a reduced ISR mRNA marker expression in 2b5ho mice. Adult gender-matched mice were injected intraperitoneally with saline or Gb (10 mg/kg). eIF2a phosphorylation was measured with Western blot and mRNA levels with qPCR in post-mortem brain tissue collected 4 or 24 hours (h) after injection. Statistical analysis was performed with two-way ANOVA (*, p<0.05, , p<0.01, *, p<0.001).

Considering its effect of increasing ATF4 expression, one would expect Gb to increase VWM pathology and disease severity. However, unexpectedly, an ameliorating effect of Gb on VWM neuropathology has recently been demonstrated in VWM (2b5ho) mice [39]. As (unpublished) part of this study, we investigated the effect of Gb on the expression of ATF4 and its regulated transcriptome in mice. The results were counterintuitive and difficult to explain. In short, we injected one dose of 10 mg/kg Gb intraperitoneally into four wildtype (wt) and four 2b5ho mice. Saline-injected wt and 2b5ho mice were used as negative controls for measuring Gb effects on ISR markers. We euthanized the mice 4 or 24 hours after injection (two mice per genotype per time point). The time points were chosen as the half-life of Gb in blood/tissue is approximately 6 hours: Gb levels are relatively high at 4 hours after injection whereas at 24 hours after injection most of the Gb has been cleared. Organs were removed, snap frozen in liquid nitrogen and stored at −80° C. Tissue samples for RNA and protein analyses were prepared as described [36]. In postmortem brain tissue we measured levels of phosphorylated eIF2a with Western blot and levels of mRNAs encoding ATF4 and ATF4-regulated targets CHOP and TRIB3 with qPCR. Based on Gb's inhibitory effect on GADD34 we expected that Gb would increase eIF2a phosphorylation and ATF4 expression. Surprisingly, the results showed the opposite: in brain tissue of Gb-injected animals levels of eIF2a phosphorylation were lower than in saline-injected animals, irrespective of the mouse genotype (FIG. 10). This reduction was transient and only observed 4 hours after Gb injection. Levels of eIF2a phosphorylation were normalized 24 hours after injection. Only in 2b5ho mice the transient decrease in eIF2a phosphorylation correlated clearly with a transient decrease in Atf4 mRNA levels. The Atf4 mRNA expression level in brain tissue from wt mice appeared to be unaffected by Gb injection, possibly because this expression was very low or absent (compare also ATF4-driven expression of Trib3 mRNA in wt and 2b5ho mice). Alternatively, the lack of statistical significance is due to the low number of animals per group (n=2). Ddit3 and Trib3 mRNA expression was reduced at both time points in Gb-injected compared to saline-injected 2b5ho mice (although statistical significance was not reached for the Trib3 mRNA reduction at 4 hours). The discrepancy between Gb effects on eIF2a phosphorylation and Atf4 mRNA expression versus Ddil3 and Trib3 mRNA expression may be a matter of differences in turnover of phosphorylation eIF2a or investigated mRNAs (and is perhaps related to the dynamics of the ISR). Alternatively, Gb may not inhibit GADD34 and may target the ISR at a different site or in a different manner as reported [40].

Abbreviations

EDTA=ethylenediaminetetraacetic acid
eIF2B=eukaryotic translation initiation factor 2B
DAPI=4',6-diaminido-2-fenylindool
GFAP=glial fibrillary acidic protein
MBP=myelin basic protein
MOG=myelin-oligodendrocyte glycoprotein
p-eIF2=phosphorylated eukaryotic initiation factor 2
PBS=phosphate-buffered saline
PFA=paraformaldehyde
PLP=proteolipid protein
RC2=radial glial cell marker 2
S100ß=Protein S100ß
UPR=unfolded protein response
VWM=Vanishing White Matter
WMD=white matter disorder
WT=wildtype

CITED ART

1 Bonkowsky J L, Nelson C, Kingston J L, Filloux F M, Mundorff M B, Srivastava R. The burden of inherited leukodystrophies in children. *Neurol* 2010; 75: 718-725

2 Vanderver A, Hussey H, Schmidt J L, Pastor W, Hoffman H J. Relative incidence of inherited white matter disorders in childhood to acquired pediatric demyelinating disorders. *Semin Pediatr Neurol* 2012; 19: 219-223

3 Gulati S, Jain P, Chakrabarty B, Kumar A, Gupta N, Kabra M. The spectrum of leukodystrophies in children: Experience at a tertiary care centre for North India. *Ann Indian Acad Neurol* 2016; 19: 332-338

4 van der Knaap M S, Pronk J C, Scheper G C. Vanishing white matter disease. *Lancet Neurol* 2006; 5: 413-423

5 Bugiani M, Boor I, Powers J M, Scheper G C, van der Knaap M S. Leukoencephalopathy with vanishing white matter: a review. *J Neuropathol Exp Neurol* 2010; 69: 987-996

6 Bugiani M, Boor I, van Kollenburg B, Postma N, Polder E, van Berkel C, van Kesteren R E, Windrem M S, Hol E M, Scheper G C, Goldman S A, van der Knaap M S. Defective glial maturation in vanishing white matter disease. *J Neuropathol Exp Neurol* 2011; 70: 69-82

7 Dooves S, Bugiani M, Postma N L, Polder E, Land N, Horan S T. van Deijk A L, van der Kreeke A, Jacobs G, Vuong C, Klooster J, Kamermans M, Wortel J, Loos M, Wisse L E, Scheper G C, Abbink T E, Heine V M, van der Knaap M S. Astrocytes are central in the pathomechanisms of vanishing white matter. *J Clin Invest* 2016; 126: 1512-1524

8 Leegwater P A, Vermeulen G, Könst A A, Naidu S, Mulders J, Visser A, Kersbergen P, Mobach D, Fonds D, van Berkel C G, Lemmers R J, Frants R R, Oudejans C B, Schutgens R B, Pronk J C, van der Knaap M S. Subunits of the translation intiation factor eIF2B are mutant in leukoencephalopathy with vanishing white matter. *Nat Genet* 2001: 29; 383-388.

9 van der Knaap M S, Wolf N I, Heine V M. Leukodystrophies five new things. *Neurol Clin Pract* 2016; 6:1-9

10 Dooves S, van der Knaap M S, Heine V M. Stem cell therapy for white matter disorders: don't forget the microenvironment! *J Inherit Metab Dis* 2016; 39: 513-518

11 Goldman S A, Nedergaard M, Windrem M S. Glial progenitor cell-based treatment and modeling of neurological disease. *Science* 2012; 338: 491-495

12 Maeder M L, Gersbach C A. Genome-editing technologies for gene and cell therapy. *Mol Ther* 2016; 24: 430-446

13 Ricca A, Rufo N, Ungari S, Morena F, Martino S, Kulik W, Alberizzi V, Bolino A, Bianchi F, Del Carro U, Biffi A, Gritti A. Combined gene/cell therapies provide long-term and pervasive rescue of multiple pathological symptoms in a murine model of globoid cell leukodystrophy. *Hum Mol Genet* 2015: 24; 3372-3389

14 Bugiani M, Postma N, Polder E, Dieleman N, Scheffer P G, Sim F J, van der Knaap M S, Boor I. Hyaluronan accumulation and arrested oligodendrocyte progenitor maturation in vanishing white matter disease. *Brain* 2013; 136: 209-222

15 Tribouillard-Tanvier D, Béringue V, Desban N, Gug F, Bach S, Voisset C, Galons H, Laude H, Vilette D, Blondel M. Antihypertensive drug guanabenz is active in vivo against both yeast and mammalian prions. *Plos One* 2008; 3: e1981

16 Tsaytler P, Harding H P, Ron D, Bertolotti A. Selective inhibition of a regulatory subunit of protein phosphatase 1 restores proteostasis. *Science* 2011; 332:91-94

17 Wang L, Popko B, Tixier E, Roos R P. Guanabenz, which enhances the unfolded protein response, ameliorates mutant SOD1-induced amyotrophic lateral sclerosis. *Neurobiol Dis* 2014; 71: 317-324

18 Ng S Y, Soh B S, Rodriguez-Muela N, Hendrickson D G, Price F, Rinn J L, Rubin L L. Genome-wide RNA-seq of human motor neurons implicates selective E R stress activation in spinal muscular atrophy. *Cell Stem Cell* 2015; 17: 569-584

19 Way S W, Podojil J R, Clayton B L, Zaremba A, Collins T L, Kunjamma R B, Robinson A P, Brugarolas P, Miller R H, Miller S D, Popko B. Pharmaceutical integrated stress response enhancement protects oligodendrocytes and provides a potential multiple sclerosis therapeutic. *Nat Commun* 2015; 6: 6532

20 Dash P K, Hylin M J, Hood K N, Orsi S A, Zhao J, Redell J B, Tsvetkov A S, Moore A N. Inhibition of eukaryotic initiation factor 2 alpha phosphatase reduces tissue damage and improves learning and memory after experimental traumatic brain injury. *J Neurotrauma* 2015; 32: 1608-1620

21 Vieira F G, Ping Q, Moreno A J, Kidd J D, Thompson K, Jiang B, et al. (2015) Guanabenz Treatment Accelerates Disease in a Mutant SOD1 Mouse Model of AIS. PLoS ONE 10(8): e0135570. https://doi.org/10.1371/journal.pone.0135570

22 Saraswat Ohri S, Mullins A, Hetman M, Whittemore S R (2014) Inhibition of GADD34, the Stress-Inducible Regulatory Subunit of the Endoplasmic Reticulum Stress Response, Does Not Enhance Functional Recovery after Spinal Cord Injury. PLoS ONE 9(11): e109703. https://doi.org/10.1371/journal.pone.0109703

23 van der Voorn J P, van Kollenburg B, Bertrand G, van Haren K, Scheper G C, Powers J M, van der Knaap M S. *Journal of Neuropathology & Experimental Neurology*, Volume 64 2005, Pages 770-775. https://doi.org/10.1097/01.jnen.0000178446.41595.3a 24 Kapur M, Monaghan C E, and Ackerman S L, Regulation of mRNA Translation in Neurons—A Matter of Life and Death. *Neuron* Vol 96, 2017, Pages 616-637. https://doi.org/10.1016/j.neuron.2017.09.057

25 Heine V M, Rowitch D H. Hedgehog signaling has a protective effect in glucocorticoid-induced mouse neonatal brain injury through an 11 beta HSD2-dependent mechanism. *J Clin Invest* 2009; 119: 267-277

26 Rivero-Gutiérrez B, Anzola A, Martinez-Augustin O, de Medina F S. Stain-free detection as loading control alternative to Ponceau and housekeeping protein immunodetection in Western blotting. *Anal Biochem* 2014; 467: 1-3

27 Gürtler A, Kunz N, Gomolka M, Hornhardt S, Friedl A A, McDonald K, Kohn J E, Posch A. Stain-free technology as a normalization tool in Western blot analysis. *Anal Biochem* 2013; 433: 105-111

28 Buffo A, Rossi F. Origin, lineage and function of cerebellar glia. *Prog Neurobiol* 2013; 109: 42-63

29 Patro N, Naik A, Patro I K. Differential temporal expression of S100 beta in developing rat brain. *Front Cell Neurosci* 2015; 9: 87

30 Ajtai B M, Kálmán M. Glial fibrillary acidic protein expression but no glial demarcation follows the lesion in the molecular layer of the cerebellum. *Brain Res* 1998; 802: 285-288

31 Adorjan I, Bindics K, Galgoczy P, Kalman M. Phases of intermediate filament composition in Bergmann glia following cerebellar injury in adult rat. *Exp Brain Res* 2014; 232: 2095-2104

32 Lafarga M, Berciano M T, Saurez Andres M A, Berciano J. Reactive astroglia-neuron relationships in the human cerebellar cortex: a quantitative, morphological and 33. immunocytochemical study in Creutzfeldt-Jakob disease. *Int J Dev Neurosci* 1993; 11: 199-213
34. Komine O, Nagaoka M, Watase K, Gutmann D H, Tanigaki K, Honjo T, Radtke F, Saito T, Chiba S, Tanaka K. The monolayer formation of Bergmann glial cells is regulated by Notch/RBP-J signaling. *Dev Biol* 2007: 311: 238-250
35. Wang X, Imura T, Sofroniew M V, Fushiki S. Loss of adenomatous polyposis coli in Bergmann glia disrupts their unique architecture and leads to cell nonautonomous neurodegeneration of cerebellar Purkinje neurons. *Glia* 2011: 59: 857-868
36. Das I, Krzyzosiak A, Schneider K, Wrabetz L, D'Antonio M, Barry N, Sigurdardottir A, Bertolotti A. Preventing proteostasis diseases by selective inhibition of a phosphatase regulatory subunit. *Science* 2015; 348: 239-242.
37. Wisse L E, Penning R, Zaal E A, et al., Proteomic and metabolomic analyses of vanishing white matter mouse astrocytes reveal deregulation of er functions, Front Cell Neurosci, 2017, 11.
38. Sekine Y, Zyryanova A, Crespillo-Casado A, et al., Stress responses. Mutations in a translation initiation factor identify the target of a memory-enhancing compound, Science, 2015, 348, 1027-30.
39. Sidrauski C, Tsai J C, Kampmann M, et al., Pharmacological dimerization and activation of the exchange factor eif2b antagonizes the integrated stress response, Elife, 2015, 4, e07314.
40. Dooves S B M, Wisse L E, Abbink T E M, van der Knaap M S, Heine V M., Bergmann glia translocation: A new disease marker for vanishing white matter identifies therapeutic effects of guanabenz treatment, Neuropathology and Applied Neurobiology, 2017, in press, doi: 10.1111/nan.12411.
41. Crespillo-Casado A, Chambers J E, Fischer P M, et al., Ppp1r15a-mediated dephosphorylation of eIF2a is unaffected by sephin1 or guanabenz, Elife, 2017, 6.

The invention claimed is:

1. A method of treatment of a human subject that has vanishing white matter, the method comprising administering the compound guanabenz to the human subject in need thereof.

2. The method of claim 1, wherein the compound is administered to the human subject orally in the form of a pill or a capsule.

3. The method of claim 1, wherein the dosage is 50 ug/kg/day-1 mg/kg/day based on the weight of the human subject to be treated.

4. The method of claim 1, wherein the dosage is 0.1-1 mg/kg/day based on the weight of the human subject to be treated.

5. The method of claim 1, wherein the dosage is 0.125-0.5 mg/kg/day based on the weight of the human subject to be treated.

* * * * *